United States Patent
Saito et al.

(10) Patent No.: US 7,625,897 B2
(45) Date of Patent: Dec. 1, 2009

(54) NON-NUCLEOSIDE REVERSE TRANSCRIPTASE INHIBITORS

(75) Inventors: Yoshihito David Saito, Chicago, IL (US); Mark Smith, San Francisco, CA (US); Zachary Kevin Sweeney, Redwood City, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/541,011

(22) Filed: Sep. 29, 2006

(65) Prior Publication Data

US 2007/0078128 A1    Apr. 5, 2007

Related U.S. Application Data

(60) Provisional application No. 60/722,335, filed on Sep. 30, 2005.

(51) Int. Cl.
C07D 253/06    (2006.01)
A61K 31/53    (2006.01)
A61P 31/18    (2006.01)

(52) U.S. Cl. ...................... 514/242; 544/182
(58) Field of Classification Search ................ 544/182; 514/242
See application file for complete search history.

(56) References Cited

U.S. PATENT DOCUMENTS

| 5,886,178 A | 3/1999 | Allen |
| 2005/0215554 A1 | 9/2005 | Dunn |

FOREIGN PATENT DOCUMENTS

WO    WO 97/02024 A1    1/1997

WO    WO 2004/085406 A1    10/2004

OTHER PUBLICATIONS

Arnold, Current Opinion in Structural Biology, 14, 716-730, 2004.*

* cited by examiner

Primary Examiner—Venkataraman Balasubramanian
(74) Attorney, Agent, or Firm—Brian L. Buckwalter

(57) ABSTRACT

The present invention provides compounds of formula I where $R^1$ to $R^4$ are as defined herein which are useful for treating or preventing an human immunodeficiency virus (HIV) infection, or treating AIDS or ARC. The invention further provides for methods of treating or preventing HIV infection with compounds according to formula I and compositions containing the same. The invention still further provides process for the preparation of compounds of formula I wherein $R^4$ is $A^1$ and $X^1$ is NH or O.

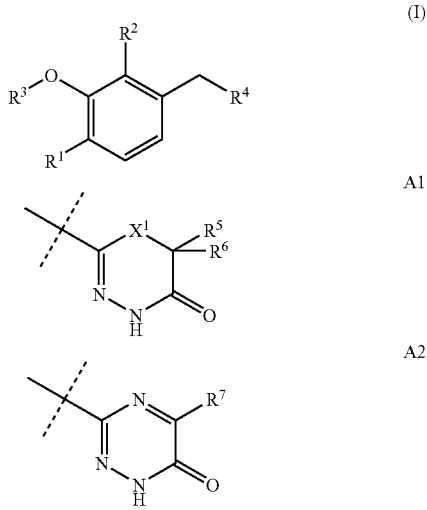

14 Claims, No Drawings

NON-NUCLEOSIDE REVERSE TRANSCRIPTASE INHIBITORS

REFERENCE TO PRIOR APPLICATIONS

This application claims the benefit of priority to U.S. Ser. No. 60/722,335 filed Sep. 30, 2005 which is hereby incorporated by reference in its entirety.

FIELD OF THE INVENTION

The invention relates to the field of antiviral therapy and, in particular, to non-nucleoside compounds that inhibit HIV reverse transcriptase and are useful for treating Human Immunodeficiency Virus (HIV) mediated diseases. The invention provides novel heterocyclic compounds according to formula I, for treatment or prophylaxis of HIV mediated diseases, AIDS or ARC, employing said compounds in monotherapy or in combination therapy.

BACKGROUND OF THE INVENTION

The human immunodeficiency virus HIV is the causative agent of acquired immunodeficiency syndrome (AIDS), a disease characterized by the destruction of the immune system, particularly of the $CD4^+$ T-cell, with attendant susceptibility to opportunistic infections. HIV infection is also associated with a precursor AIDs-related complex (ARC), a syndrome characterized by symptoms such as persistent generalized lymphadenopathy, fever and weight loss. Two genetically distinct types of HIV have been identified, HIV-1 and HIV-2 (P. Lemey et al., *Proc. Nat. Acad. Sci. USA* 2003 100(11):6588-692). Reference to HIV and/or HIV reverse transcriptase herein should be understood to refer to HIV-1 and a reverse transcriptase expressed by the HIV-1 subtype.

In common with other retroviruses, the HIV genome encodes protein precursors known as gag and gag-pol which are processed by a viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two viral enzymes crucial for the production of viral proteins: HIV protease and HIV reverse transcriptase. (J. S. G. Montaner et al. "Antiretroviral therapy: 'the state of the art'", *Biomed. & Pharmacother.* 1999 53:63-72; R. W. Shafer and D. A. Vuitton, "Highly active retroviral therapy (HAART) for the treatment of infection with human immunodeficiency virus type", *Biomed. & Pharmacother.* 1999 53 :73-86; E. De Clercq, "New Developments in Anti-HIV" *Chemotherap. Curr. Med. Chem.* 2001 8:1543-1572). Two general classes of RTI inhibitors have been identified: nucleoside reverse transcriptase inhibitors (NRTI) and non-nucleoside reverse transcriptase inhibitors.

NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation.

NNRTIs were first discovered in 1989. NNRTIs are allosteric inhibitors which bind reversibly at a non-substrate-binding site on the HIV reverse transcriptase thereby altering the shape of the active site or blocking polymerase activity (R. W. Buckheit, Jr., "Non-nucleoside reverse transcriptase inhibitors: perspectives for novel therapeutic compounds and strategies for treatment of HIV infection", *Expert Opin. Investig. Drugs* 2001 10(8)1423-1442; E. De Clercq, "The role of non-nucleoside reverse transcriptase inhibitors (NNRTIs) in the therapy of HIV infection", *Antiviral Res.* 1998 38:153-179; E. De Clercq, "New Developments in Anti-HIV Chemotherapy", *Current Medicinal Chem.* 2001 8(13):1543-1572; G. Moyle, "The Emerging Roles of Non-Nucleoside Reverse Transcriptase Inhibitors in Antiviral Therapy", *Drugs* 2001 61(1): 19-26). Although over thirty structural classes of NNRTIs have been identified in the laboratory, only three compounds have been approved for HIV therapy: efavirenz, nevirapine and delavirdine.

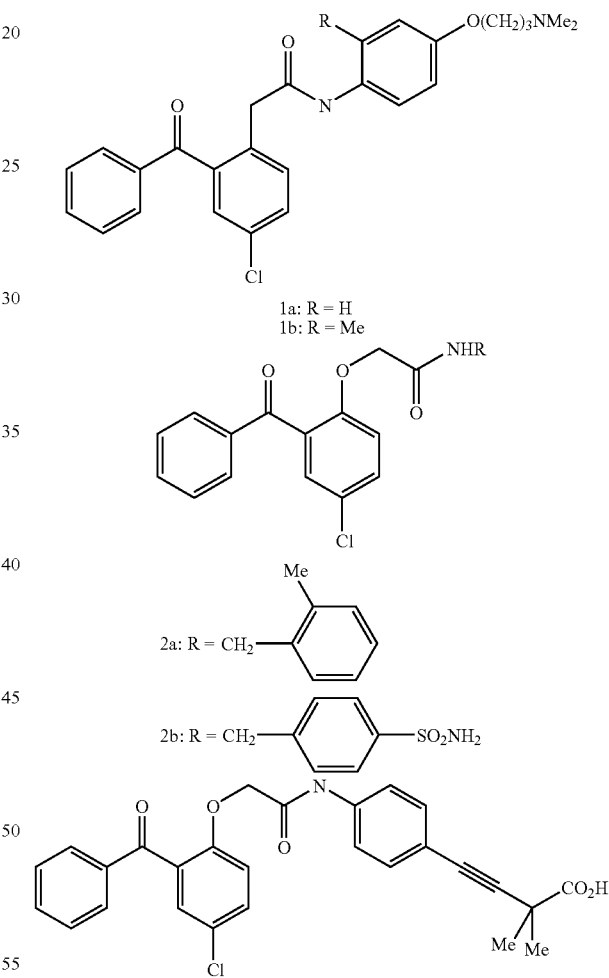

2-Benzoyl phenyl-N-[phenyl]-acetamide compounds 1a and 1b have been shown to inhibit HIV-1 reverse transcriptase (P. G. Wyatt et al., *J. Med. Chem.* 1995 38(10):1657-1665). Further screening identified related compounds, e.g. 2-benzoyl phenyloxy-N-[phenyl]-acetamide, 2a, and a sulfonamide derivative 2b which also inhibited reverse transcriptase (J. H. Chan et al., *J. Med Chem.* 2004 47(5):1175-1182; C. L. Webster et al., WO01/17982). P. Bonneau et al. in US 20060069261 published Mar. 30, 2006 disclose 4-{4-[2-(2- benzoyl-phenoxy)-acetylamino]-phenyl}-2,2-dimethyl-but-3-ynoic acid compounds 3 which are inhibitors of HIV reverse transcriptase.

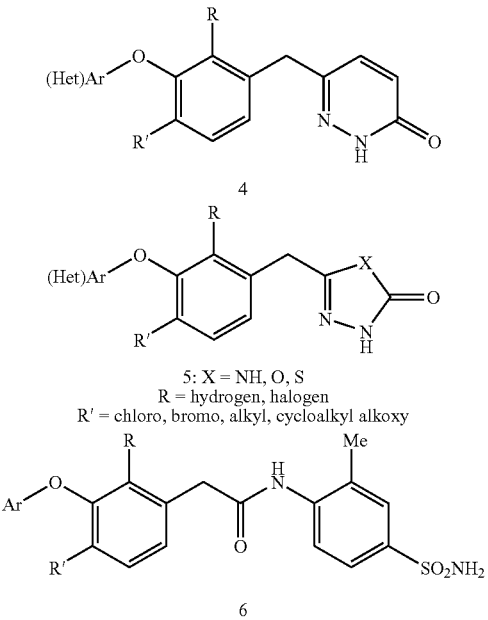

5: X = NH, O, S
R = hydrogen, halogen
R' = chloro, bromo, alkyl, cycloalkyl alkoxy Pyridazinone non-nucleoside reverse transcriptase inhibitors 4 have been described by J. P. Dunn et al. in U.S. Publication filed Mar. 23, 2004 and by J. P. Dunn et al. in U.S. Publication No. 2005021554 filed Mar. 22, 2005. 5-Aralkyl-2,4-dihydro-[1,2,4]triazol-3-one, 5-aralkyl-3H-[1,3,4]oxadiazol-2-one and 5-aralkyl-3H-[1,3,4]thiadiazol-2-one non-nucleoside reverse transcriptase inhibitors 5 have been disclosed by J. P. Dunn et al. in U.S. Publication No. 20040192704 filed Mar. 23, 2004 and by J. P. Dunn et al. in U.S. Publication No. 20060025462 filed Jun. 27, 2005. Phenylacetamide non-nucleoside reverse transcriptase inhibitors 6 have been disclosed by J. P. Dunn et aL in U.S. Pub. No. 20050239881 published Oct. 27, 2005 and methods for treating retroviral infection with phenylacetamide compounds have been disclosed by J. P. Dunn et al. in U.S. Publication No. 20050239880 published Oct. 27, 2005; T. Mirzadegan and T. Silva in U.S. Ser. No. 60/728,443 filed Oct. 19, 2005; and Z. K. Sweeney and T. Silva in U.S. Ser. No 60/728,609 Oct. 19, 2005. These applications are hereby incorporated by reference in their entirety.

In WO2006/067587 published Jun. 26, 2006, L. H. Jones et al. disclose biaryl ether derivatives and compositions containing them which bind to the enzyme reverse transcriptase and are modulators, especially inhibitors, thereof.

SUMMARY OF THE INVENTION

The present invention relates to compounds of formula I wherein
X$^1$ is O, NR$^8$ or CH$_2$;
R$^1$ is hydrogen, halogen, C$_{1-6}$ alkyl or C$_{1-6}$ alkoxy;
R$^2$ is hydrogen or halogen;
R$^3$ is phenyl optionally substituted with one to three substituents independently selected from the group consisting of C$_{1-6}$ alkyl, C$_{1-6}$ haloalkyl, C$_{3-8}$ cycloalkyl, halogen, cyano or nitro;
R$^4$ is A1 or A2;
R$^5$ and R$^6$ are independently hydrogen, C$_{1-10}$ alkyl, C$_{1-6}$ haloalkyl, hydroxy-C$_{1-6}$ alkyl or phenyl optionally substituted with 1 to 3 groups independently selected in each occurrence from the group consisting of C$_{1-6}$ alkyl, C$_{1-6}$ alkoxy, C$_{1-6}$ haloalkyl, halogen, hydoxy, nitro and cyano, or, R$^5$ and R$^6$ together are (CH$_2$)$_n$;
R$^7$ is hydrogen, C$_{1-10}$ alkyl or phenyl;
R$^8$ is hydrogen or C$_{1-6}$ alkyl;
n is 2 to 4; and
pharmaceutically acceptable salts thereof.

Compounds of formula I are useful inhibitors of HIV-1 reverse transcriptase and afford a method for prevention or treatment of HIV-1 infections or the treatment of AIDS and/or ARC. HIV undergoes facile mutations of its genetic code resulting in strains with reduced susceptibility to therapy with current therapeutic options. The present invention also relates to compositions containing compounds of formula I useful for the prevention and treatment of HIV-1 infections and the treatment of AIDS and/or ARC. The present invention further relates to compounds of formula I which are useful in mono therapy or combination therapy with other anti-viral agents.

DETAILED DESCRIPTION OF THE INVENTION

In one embodiment of the present invention there is provided a compound according to formula I wherein R$^1$, R$^2$, R$^3$, R$^4$, R$^5$, R$^6$, R$^7$, R$^8$, X$^1$ and n are as defined herein above.

In another embodiment of the present invention there is provided a compound according to formula I wherein R$^4$ is A1, R$^8$ is hydrogen and R$^1$, R$^2$, R$^3$, R$^5$, R$^6$, X$^1$ and n are as defined herein above.

In another embodiment of the present invention there is provided a compound according to formula I wherein $R^1$ is bromo, chloro, methyl or ethyl, $R^2$ is hydrogen or fluoride, $R^4$ is A1, $R^8$ is hydrogen and $R^3$, $R^5$, $R^6$, $X^1$ and n are as defined herein above.

In another embodiment of the present invention there is provided a compound according to formula 1 wherein $R^1$ is bromo, chloro, methyl or ethyl, $R^2$ is hydrogen or fluorine, $R^3$ is phenyl substituted with one or two substituents, $R^4$ is A1, $R^8$ is hydrogen and $R^5$, $R^6$, $X^1$ and n are as defined herein above. The phenyl substituents for $R^3$ in this embodiment are independently selected from halogen, cyano or haloalkyl.

In another embodiment of the present invention there is provided a compound according to formula 1 wherein $R^1$ is bromo, chloro, methyl or ethyl, $R^2$ is hydrogen or fluoride, $R^3$ is 3,5-disubstituted phenyl, $R^4$ is A1, $R^8$ is hydrogen and $R^5$, $R^6$, $X^1$ and n are as defined herein above. The phenyl substituents for $R^3$ in this embodiment are independently selected from halogen, cyano or haloalkyl.

In another embodiment of the present invention there is provided a compound according to formula 1 wherein $R^1$ is bromo, chloro, methyl or ethyl, $R^2$ is hydrogen or fluoride, $R^3$ is 2,5-di-substituted phenyl which substituents are independently selected from the group consisting of halogen, cyano or haloalkyl, $R^4$ is A1, $R^8$ is hydrogen and $R^5$, $R^6$, $X^1$ and n are as defined herein above.

In another embodiment of the present invention there is provided a compound according to formula 1 wherein $R^1$ is bromo, chloro, methyl or ethyl, $R^2$ is hydrogen or fluoride, $R^3$ is 2,3,5-tri substituted phenyl, $R^4$ is A1, R8 is hydrogen, and $R^5$, $R^6$, $X^1$ and n are as defined herein above.

The phenyl substituents for $R^3$ in this embodiment are independently selected from halogen, cyano or haloalkyl.

In another embodiment of the present invention there is provided a compound according to formula I wherein $X^1$ is O or $NR^8$, $R^1$ is bromo, chloro, methyl or ethyl, $R^2$ is hydrogen or fluoride, $R^4$ is A1, $R^8$ is hydrogen and $R^3$, $R^5$, $R^6$ and n are as defined herein above.

In another embodiment of present invention there is provided a compound according to formula I wherein $X^1$ is O or $NR^8$, $R^1$ is bromo, chloro, methyl or ethyl, $R^2$ is hydrogen or fluoride, $R^3$ is mono- or di-substituted phenyl, $R^4$ is A1, $R^8$ is hydrogen and $R^3$, $R^5$, $R^6$ and n are as defined herein above. The phenyl substituents for $R^3$ in this embodiment are independently selected from halogen, cyano or haloalkyl.

In another embodiment of the present invention there is provided a compound according to formula I wherein $R^4$ is A2, and $R^1$, $R^2$, $R^3$ and $R^7$ are as defined herein above.

In another embodiment of the present invention there is provided a compound according to formula I wherein $R^1$ is bromo, chloro, methyl or ethyl, $R^2$ is hydrogen or fluoride, $R^4$ is A2, $R^3$ and $R^7$ are as defined herein above.

In another embodiment of the present invention there is provided a compound according to formula I wherein $R^1$ is bromo, chloro, methyl or ethyl, $R^2$ is hydrogen or fluoride, $R^3$ is phenyl substituted with one or two substituents independently selected from the group consisting of halogen, cyano and haloalkyl $R^4$ is A2, $R^3$ and $R^7$ are as defined herein above.

In another embodiment of the present invention there is provided a compound according to formula I wherein $R^1$ is bromo, chloro, methyl or ethyl, $R^2$ is hydrogen or fluoride, $R^3$ is 3,5-disubstituted phenyl which subsituents are independently selected from the group consisting of halogen, cyano and haloalkyl, $R^4$ is A2, $R^3$ and $R^7$ are as defined herein above.

In another embodiment of the present invention there is provided a compound according to formula I wherein $R^1$ is bromo, chloro, methyl or ethyl, $R^2$ is hydrogen or fluoride, $R^3$ is 2,5-disubstituted phenyl which substituents are independently selected from the group consisting of halogen, cyano and haloalkyl, $R^4$ is A2, $R^3$ and $R^7$ are as defined herein above.

In another embodiment of the present invention there is provided a compound according to formula I wherein $R^1$ is bromo, chloro, methyl or ethyl, $R^2$ is hydrogen or fluoride, $R^3$ is 2,3,5-trisubstituted phenyl which substituents are independently selected from the group consisting of halogen, cyano and haloalkyl, $R^4$ is A2, $R^3$ and $R^7$ are as defined herein above.

In another embodiment of the present invention there is provided a method for treating or preventing an human immunodeficiency virus (HIV) infection, or treating AIDS or ARC, in a patient in need thereof which comprises administering to the patient a therapeutically effective amount of a compound according to formula I wherein $R^1$, $R^2$, $R^3$, $R^4$, $R^5$, $R^6$, $R^7$, $R^8$, $X^1$ and n are as defined herein above.

In another embodiment of the present invention there is provided a method for treating or preventing an human immunodeficiency virus (HIV) infection, or treating AIDS or ARC, in a patient in need thereof which comprises co-administering to the patient a therapeutically effective amount of a compound according to formula I wherein $R^1$, $R^2$, $R^3$, $R^4$, $R^5$, $R^6$, $R^7$, $R^8$, $X^1$ and n are as defined herein above and at least one compound selected from the group consisting of HIV nucleoside reverse transcriptase inhibitors, HIV non-nucleoside reverse transcriptase inhibitors, HIV protease inhibitors and viral fusion inhibitors.

In another embodiment of the present invention there is provided a method for treating or preventing an human immunodeficiency virus (HIV) infection, or treating AIDS or ARC, in a patient in need thereof which comprises co-administering to the patient a therapeutically effective amount of a compound according to formula I wherein $R^1$, $R^2$, $R^3$, $R^4$, $R^5$, $R^6$, $R^7$, $R^8$, $X^1$ and n are as defined herein above and at least one compound which compound is efavirenz, nevirapine or delavirdine, zidovudine, didanosin, zalcitabine, stavudine, lamivudine, abacavir, adefovir, dipivoxil, saquinavir, ritonavir, nelfinavir, indinavir, amprenavir and lopinavir and/or T20.

In another embodiment of the present invention there is provided a method for inhibiting a retrovirus reverse transcriptase comprising administering to the patient a therapeutically effective amount of a compound according to formula I wherein $R^1$, $R^2$, $R^3$, $R^4$, $R^5$, $R^6$, $R^7$, $R^8$, $X^1$ and n are as defined herein above.

In another embodiment of the present invention there is provided a method for inhibiting a retrovirus reverse transcriptase with at least one mutation compared to wild type virus comprising administering to the patient a therapeutically effective amount of a compound according to formula I wherein $R^1$, $R^2$, $R^3$, $R^4$, $R^5$, $R^6$, $R^7$, $R^8$, $X^1$ and n are as defined herein above.

In another embodiment of the present invention there is provided a method for treating or preventing an human immunodeficiency virus (HIV) infection, or treating AIDS or ARC, in a patient infected with at least one strain of HIV exhibiting reduced susceptibility to efavirenz, nevirapine or delavirdine, comprising administering a therapeutically effective amount of a compound according to formula I wherein $R^1$, $R^2$, $R^3$, $R^4$, $R^5$, $R^6$, $R^7$, $R^8$, $X^1$ and n are as defined herein above.

In another embodiment of the present invention there is provided a pharmaceutical composition or treating or preventing an human immunodeficiency virus (HIV) infection, or treating AIDS or ARC comprising a compound according formula I wherein $R^1$, $R^2$, $R^3$, $R^4$, $R^5$, $R^6$, $R^7$, $R^8$, $X^1$ and n are as defined herein above admixed with at least one pharmaceutically acceptable carrier, diluent or excipient.

In another embodiment of the present invention there is provided a process for the preparation of a compound according to formula I wherein either (i) $R^4$ is A1, $X^1$ is $NR^8$ and $R^8$ is hydrogen, or (ii) $R^4$ is A2 and $R^3$, $R^5$, $R^6$ and $R^7$ are as defined in claim 1 from a carboxylic acid derivative as depicted in SCHEME 1 (13 to 10). In the first step of the process a carboxylic acid or a carboxylic acid derivative is converted to an acyl hydrazide (15a). The carboxylic acid derivative commonly is an ester, an acid chloride or anhydride. The second step requires the conversion of an amide to a thioamide 15b. This conversion is frequently carried out with Lawesson's reagent although other reagents, e.g., $P_2S_5$ can also be used. The third step is the condensation of the thioamide and hydrazine to afford a 4,5-dihydro-1H-[1,2,4]triazin-6-one which optionally can be oxidized to the corresponding 1H-[1,2,4]triazin-6-one 16 when at least one of $R^5$ and/or $R^6$ is/(are) hydrogen.

In another embodiment of the present invention there is provided a process for the preparation of a compound according to formula I wherein $R^4$ is A1, $X^1$ is O and $R^1$, $R^2$, $R^3$, $R^5$, $R^6$ and n are as defined in claim 1 from a carboxylic acid derivative as depicted in SCHEME 2 (17a to 19b).

In another embodiment of the present invention there is provided a compound according to formula I which compound is selected from compounds I-1 to I-30 in TABLE 1 or compounds II-1 to II-6 in TABLE 2

In the first step of the process a carboxylic acid or a carboxylic acid derivative is converted to an acyl hydrazide (15b). The carboxylic acid derivative commonly is an ester, an acid chloride or anhydride. The second step entails benzylation of the acyl hydrazide 15b by reductive alkylation with an aryl aldehyde and subsequent acylation with a 2-halo alkanoyl halide to afford 18. The third step in this embodiment of the invention is an intra-molecular cyclization by displacement of the 2-halo leaving group by the oxygen in the enol tautomer of the carboxamide to afford 19, The final step is the debenzylation of the N-benzyl-4H-[1,3,4]oxadiazin-5-one.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the first definition provided in the Summary of the Invention.

"Optional" or "optionally" means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1 iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "cyano" as used herein refers to a carbon linked to a nitrogen by a triple bond, i.e., —C≡N.

The term "halogen" or "halo" as used herein means fluorine, chlorine, bromine, or iodine.

The term "2-haloalkanoyl" as used herein refers to the group R'R"C(Cl)C(O)— wherein R' and R" are independently hydrogen or $C_{1-6}$ alkyl as defined above.

The terms "hydroxyalkyl" and "alkoxyalkyl" as used herein denotes the radical R'R" where R' is a hydroxy radical or a alkoxy radical respectively and R" is alkylene as defined herein and the attachment point of the hydroxyalkyl radical will be on the alkylene radical and the hydroxyl or alkoxy radical can be attached at any carbon atom on the alkylene chain.

The term "alkylene" as used herein denotes a divalent saturated linear hydrocarbon radical of 1 to 8 carbon atoms [—$(CH_2)_n$— wherein n is one to eight] or a branched saturated divalent hydrocarbon radical of 3 to 8 carbon atoms, unless otherwise indicated. Examples of alkylene radicals include, but are not limited to, methylene, ethylene, propylene, 2-methyl-propylene, butylene, 2-ethylbutylene.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a substance whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Compounds of formula I which are basic can form pharmaceutically acceptable acid addition salts with inorganic acids such as hydrohalic acids (e.g. hydrochloric acid and hydrobromic acid), sulphuric acid, nitric acid and phosphoric acid, and the like, and with organic acids (e.g. with acetic acid, tartaric acid, succinic acid, fumaric acid, maleic acid, malic acid, salicylic acid, citric acid, methanesulphonic acid and p-toluenesulfonic acid, and the like).

The term "coupling reagent" as used herein refers to a reagent or reagents which are used to couple a carboxylic acid and an amine. These reagents are well known in the art and coupling procedures have been extensively optimized for peptide synthesis and these reagents are applicable to prepare compounds of the present invention. Typical coupling reagents include, but are not limited to, DCC, NDCC/N-hydroxysuccinimide or HOBT, CDI, O-(benzotriazol-1-yl)-N,N,N',N'-tetramethyl-uronium tetrafluoroborate/NMM, O-(benzotriazol-1-yl)-N,N,N',N'-tetramethyl-uronium tetrafluoroborate/DIPEA, N,N'-thionyldiimidazole or $Ph_3P/CCl_4$. Couplings are carried out at temperatures between −20 and 200° C., but preferably at temperatures between −10 and 160° C. and most preferably between 2o and 40° C.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

Lawesson's reagent is [2,4-bis-(4-methoxyphenyl)-1,3-dithia-2,4-diphosphetane-2,4-disulfide.

The term "wild type" as used herein refers to the HIV virus strain which possesses the dominant genotype which naturally occurs in the normal population which has not been exposed to reverse transcriptase inhibitors. The term "wild type reverse transcriptase" used herein has refers to the reverse transcriptase expressed by the wild type strain which has been sequenced and deposited in the SwissProt database with an accession number P03366.

The term "reduced susceptibility" as used herein refers to about a 10 fold, or greater, change in sensitivity of a particular viral isolate compared to the sensitivity exhibited by the wild type virus in the same experimental system.

The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA. Recent progress is development of RTI and PI inhibitors have been reviewed: F. M. Uckun and O. J. D'Cruz, *Exp. Opin. Ther. Pat.* 2006 16:265-293, L. Menendez-Arias, *Eur. Pharmacother.* 2006 94-96 and S. Rusconi and O. Vigano, *Future Drugs* 2006 3(1):79-88.

Typical suitable NRTIs include zidovudine (AZT; RETROVIR®) from GSK; didanosine (ddI; VIDEX®) from Bristol-Myers Squibb Co. (BMS); zalcitabine (ddC; HIVID®) from Roche; stavudine (d4T; ZERIT®) from BMS; lamivudine (3TC; EPIVIR®) from GSK; abacavir (1592U89; ZIAGEN®) disclosed in WO96/30025 and available from GSK; adefovir dipivoxil (bis(POM)-PMEA; PREVON®) Gilead Sciences; lobucavir (BMS-180194), a nucleoside reverse transcriptase inhibitor disclosed in EP-0358154 and EP-0736533 and under development by BMS; BCH-10652, a reverse transcriptase inhibitor (in the form of a racemic mixture of BCH-10618 and BCH-10619) under development by Biochem Pharma; emitricitabine [(−)-FTC] licensed from Emory University under Emory Univ. U.S. Pat. No. 5,814, 639 and under development by Gilead Sciences, Inc; Evucitabine (β-L-D4FC; β-L-2', 3'-dideoxy-5-fluoro-cytidene) licensed by Yale University to Vion Pharmaceuticals; DAPD, the purine nucleoside, (−)-β-D-2,6,-diamino-purine dioxolane disclosed in EP-0656778 and licensed by Emory University and the University of Georgia to Triangle Pharmaceuticals; and lodenosine (FddA), 9-(2,3-dideoxy-2-fluoro-β-D-threo-pentofuranosyl)adenine, an acid stable purine-based reverse transcriptase inhibitor discovered by the NIH and under development by U.S. Bioscience Inc.

Three NNRTIs have been approved in the USA: nevirapine (BI-RG-587; VIRAMUNE®) available from Boehringer Ingelheim (BI); delaviradine (BHAP, U-90152; RESCRIPTOR®) available from Pfizer; efavirenz (DMP-266, SUSTIVA®) a benzoxazin-2-one from BMS. Other NNRTIs currently under investigation include PNU-142721, a furopyridine-thio-pyrimide under development by Pfizer; capravirine (S-1153 or AG-1549; 5-(3,5-dichlorophenyl)-thio4-isopropyl-1-(4-pyridyl)methyl-1H-imidazol-2-ylmethyl carbonate) by Shionogi and Pfizer; emivirine [MKC442; (1-(ethoxy-methyl)-5-(1-methylethyl)-6-(phenylmethyl)-(2,4(1H,3H)-pyrimidinedione)] by Mitsubishi Chemical Co. and Triangle Pharmaceuticals; (+)-calanolide A (NSC-675451) and B, coumarin derivatives disclosed in NIH U.S. Pat. No. 5,489,697, licensed to Sarawak/Advanced Life Sciences; etravirine (TMC-125; 4-[6-amino-5-bromo-2-(4-cyano-phenylamino)-pyrimidin-4-yloxy]-3,5-dimethyl-benzonitrile) and DAPY (TMC 120; 4-{4-[4-((E)-2-cyano-vinyl)-2,6-dimethyl-phenylamino]-pyrimidin-2-ylamino}-benzonitrile) by Tibotec-Virco and Johnson & Johnson; BILR-355 BS (12-ethyl-8-[2-(1-hydroxy-quinolin4-yloxy)-ethyl]-5-methyl-11,12-dihydro-5H-1,5,10,12-tetraaza-dibenzo[a,e]cycloocten-6-one by Boehringer-Ingleheim; PHI-236 (7-bromo-3-[2-(2,5-dimethoxy-phenyl)-ethyl]-3,4-dihydro-1H-pyrido[1,2-a][1,3,5]triazine-2-thione) and PHI-443 (1-(5-bromo-pyridin-2-yl)-3-(2-thiophen-2-yl-ethyl)-thiourea) by Paradigm Pharmaceuticals.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN® as well as nonpeptide protease inhibitors e.g., VIRACEPT®.

Typical suitable PIs include saquinavir available in hard gel capsules as INVIRASE® and in soft gel capsules as FORTOVASE® from Roche; ritonavir (ABT-538) available as NORVIR-from Abbott Laboratories; Lopinavir (ABT-378) also available from Abbot; KALETRA®), is co-formulation lopinavir and a sub-therapeutic dose of ritonavir available from Abbott Laboratories; indinavir (MK-639) available as CRIXIVAN® from Merck & Co.; nelfnavir (AG-1343) available as VIRACEPT® from Agouron Pharmaceuticals, Inc.; amprenavir (141W94) available as AGENERASE® from Vertex Pharmaceuticals, Inc. and GSK; tipranavir (PNU-140690) available as APTIVUS® from BI; lasinavir (BMS-234475/CGP-61755) by BMS; BMS-2322623, an azapeptide under development by BMS as a 2nd-generation HIV-1 PI; GW-640385X (VX-385) under development in a collaboration between GSK and Vertex; AG-001859 in preclinical development by Agouron/Pfizer; SM-309515 under development by Sumitomo Pharmaceuticals.

Additional PIs in preclinical development include N-cycloalkylglycines by BMS, α-hydroxyarylbutanamides by Enanta Pharmaceuticals; α-hydroxy-γ-[[(carbocyclic- or heterocyclic-substituted)amino)carbonyl]alkanamide derivatives; γ-hydroxy-2-(fluoroalkylaminocarbonyl)-1-piperazinepentanamides by Merck; dihydropyrone derivatives and α- and β-amino acid hydroxyethylamino sulfonamides by Pfizer; and N-amino acid substituted L-lysine derivatives by Procyon.

Entry of HIV into target cells requires CD4 cell surface receptor and the CCR5 (M-tropic strains)and CXCR4 (T-tropic strains) chemokine co-receptors. Chemokine antagonize which block viral binding to the chemokines are useful inhibitors of viral infection. Takeda's identified TAK-779 as a potential CCR5 antagonist. (M. Shiraishi et al., *J. Med. Chem.* 2000 43(10):2049-2063; M. Babba et al. *Proc.*

*Nat. Acad Sci. USA* 1999 96:5698-5703) and TAK-220 (C. Tremblay et al. *Antimicrob. Agents Chemother.* 2005 49(8): 3483-3485). WO0039125 (D. R. Armour et al.) and WO0190106 (M. Perros et al.) disclose heterocyclic compounds that are potent and selective CCR5 antagonists. Miraviroc (UK427,857; MVC) has advanced by Pfizer to phase III clinical trials and show activity against HIV-1 isolates and laboratory strains (P. Dorr et al., *Antimicrob. Agents Chemother.* 2005 49(11):4721-4732; A. Wood and D. Armour, *Prog. Med. Chem.* 2005 43:239-271; C. Watson et al., *Mol. Pharm.* 2005 67(4):1268-1282; M. J. Macartney et al., $43^{rd}$ *Intersci. Conf: Antimicrob. Agents Chemother.* Sep. 14-17, 2003, Abstract H-875). Schering has advanced Sch-351125 (SCH-C) into Phase I/II clinical studies and reported the advance of a more potent follow-up compound, Vicroviroc (Sch417690, SCH-D) into Phase I studies. (S. W. McCrombie et al., WO00066559; B. M. Baroudy et al. WO00066558; A. Palani et al., *J Med. Chem.* 2001 44(21): 3339-3342; J. R. Tagat et al., *J Med. Chem.* 2001 44(21): 3343-3346; J. A. Esté, *Cur. Opin. Invest. Drugs* 2002 3(3): 379-383; J. M. Struzki et al. *Proc. Nat. Acad Sci. USA* 2001 98:12718-12723). Merck has disclosed the preparation of (2S)-2-(3-chlorophenyl)-1-N-(methyl)-N-(phenylsulfonyl) amino]4-[spiro(2,3-dihydrobenzothiophene-3,4'-piperidin-1'-yl)butane S-oxide (1) and related derivatives with good affinity for the CCR5 receptor and potent-HIV activity. (P. E. Finke et al., *Bioorg. Med. Chem. Lett.,* 2001 11:265-270; P. E. Finke et al., *Bioorg. Med. Chem. Lett.,* 2001 11:2469-2475; P. E. Finke et al., *Bioorg. Med. Chem. Lett.,* 2001 11:2475-2479; J. J. Hale et al., *Bioorg. Med. Chem. Lett.,* 2001 11:2741-22745; D. Kim et al., *Bioorg. Med. Chem. Lett.,* 2001 11:3099-3102) C. L. Lynch et al. *Org Lett.* 2003 5:2473-2475; R. S. Veazey et al. *J. Exp. Med.* 2003 198:1551-1562. GSK-873140 (ONO-4128, E-913, AK-602) was identified in a program initiated at Kumamoto University (K. Maeda et al. *J. Biol. Chem.* 2001 276:35194-35200; H. Nakata et al. *J Virol.* 2005 79(4):2087-2096) and has been advanced to clinical trials. In WO00/166525; WO00/187839; WO02/076948; WO02/076948; WO02/079156, WO2002070749, WO2003080574, WO2003042178, WO2004056773, WO2004018425 Astra Zeneca disclose 4-amino piperidine compounds which are CCR5 antagonists. In U.S. Publication No. 20050176703 published August 11, 2005, S. D. Gabriel and D. M. Rotstein disclosed heterocyclic CCR5 antagonist capable of prevent HIV cell entry. In U.S. Publication No. 20060014767 published Jan. 19, 2006, E. K. Lee et al. disclosed heterocyclic CCR5 antagonist capable of prevent HIV cell entry.

Attachment Inhibitors effectively block interaction between viral envelope proteins and chemokine receptors or CD40 protein. TNX-355 is a humanized IgG4 monoclonal antibody that binds to a conformational epitope on domain 2 of CD4. (L. C. Burkly et al., *J. Immunol.* 1992 149:1779-87) TNX-355 can inhibit viral attachment of CCR5-, CXCR4- and dual/mixed tropic HIV-1 strains. (E. Godofsky et al., In Vitro Activity of the Humanized Anti-CD4 Monoclonal Antibody, TNX-355, against CCR5, CXCR4, and Dual-Tropic Isolates and Synergy with Enfuvirtide, 45th Annual Interscience Conference on Antimicrobial Agents and Chemotherapy (ICAA C). Dec. 16-19, 2005, Washington DC. Abstract # 3844; D. Norris et al. TNX-355 in Combination with Optimized Background Regime (OBR) Exhibits Greater Antiviral Activity than OBR Alone in HIV-Treatment Experienced Patients, 45th Annual Interscience Conference on Antimicrobial Agents and Chemotherapy (ICAAC). Dec. 16-19, 2005, Washington DC. Abstract # 4020.)

Macromolecular therapeutics including antibodies, soluble receptors and biologically active fragments thereof have become an increasingly important adjunct to conventional low molecular weight drugs. (O. H. Brekke and I. Sandlie *Nature Review Drug Discov.* 2003 2:52-62; A. M. Reichert *Nature Biotech.* 2001 19:819-821) Antibodies with high specificity and affinity can be targeted at extra-cellular proteins essential for viral cell fusion. CD4, CCR5 and CXCR4 have been targets for antibodies which inhibit viral fusion.

V. Roschke et al. (Characterization of a Panel of Novel Human Monoclonal Antibodies that Specifically Antagonize CCR5 and Block HIV-1 Entry, 44th Annual Interscience Conference on Antimicrobial Agents and Chemotherapy (ICAAC). Oct. 29, 2004, Washington DC. Abstract # 2871) have disclosed monoclonal antibodies which bind to the CCR5 receptor and inhibit HIV entry into cells expressing the CCR5 receptor. L. Wu and C. R MacKay disclose in U.S. Ser. No 09/870,932 filed May 30, 2001 disclose monoclonal antibodies 5C7 and 2D7 which bind to the CCR5 receptor in a manner capable of inhibiting HIV infection of a cell. W. C. Olsen et al. (*J. Virol.* 1999 73(5):4145-4155) disclose monoclonal antibodies capable of inhibiting (i) HIV-1 cell entry, (ii) HIV-1 envelope-mediated membrane fusion, (iii) gp120 binding to CCR5 and (iv) CC-chemokine activity. Synergism between the anti-CCR5 antibody Pro140 and low molecular weight CCR5 antagonists have been disclosed by Murga et al. (3rd IAS Conference on HIV Pathogenesis and Treatment, Abstract TuOa.02.06. Jul. 24-27, 2005, Rio de Janeiro, Brazil) Anti-CCR5 antibodies have been isolated which inhibit HIV-1 cell entry also have been disclosed by M. Brandt et al. in U.S. Ser. No. 11/394,439 filed Mar. 31, 2006.

FUZEON® (T-20, DP-178, pentafuside) is disclosed in U.S. Pat. No. 5,464,933. T-20 and an analog, T-1249, are analogs of HIV gp41 fragment which are effectively inhibit a conformational change required for HIV fusion. T-20 has been approved and is available from Roche and Trimeris. FUZEON is administered as a continuous sc infusion or injection in combination therapy with other classes of anti HIV drugs.

Other antiviral agents which may be useful in HIV therapy include hydroxyurea, ribavirin, IL-2, IL-12, pentafuside. Hydroyurea (Droxia), a ribonucleoside triphosphate reductase inhibitor, the enzyme involved in the activation of T-cells, was discovered at the NCI and is under development by Bristol-Myers Squibb; in preclinical studies, it was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN® (aldesleukin) from Chiron Corp. as a lyophilized powder for IV infusion or sc administration. IL-12 is disclosed in WO96/25171 and is available from Roche and Wyeth Pharmaceuticals. Ribavirin, 1-β-D-ribofuranosyl-1H-1,2,4-triazole-3-carboxamide, is described in U.S. Pat. No. 4,211,771 and is available from ICN Pharmaceuticals.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include: (a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is preferred unless there is intolerance to PIs. Drug compliance is essential. The CD4+ and HIV-1-RNA plasma levels should be monitored every 3-6 months. Should viral load plateau, a fourth drug, e.g., one PI or one NNRTI could be added.

Abbreviations used in this application include: acetyl (Ac), acetic acid (HOAc), azo-bis-isobutyrylnitrile (AIBN), 1-N-hydroxybenzotriazole (HOBT), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo[5.4.0]undec-7-ene (DBU), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), d-iso-propyl ethyl amine (DIPEA, Hunig's Base), pyridine (pyr), di-iso-butylaluminumhydride (DIBAL-H), room temperature, rt or RT, N,N-dimethyl acetamide (DMA), tert-butyldimethylsilyl or t-$BuMe_2Si$, (TBDMS), 4-N,N-dimethylaminopyridine (DMAP), triethylamine ($Et_3N$ or TEA), N,N-dimethylformamide (DMF), triflate or $CF_3SO_2$— (Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether ($Et_2O$), trimethylsilyl or $Me_3$Si (TMS), ethyl (Et), p-toluenesulfonic acid monohydrate (TsOH or pTsOH), lithium hexamethyl disilazane (LiHMDS), 4-Me-$C_6H_4SO_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

COMPOUNDS AND PREPARATION

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, $2^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be recognized by one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and including, but not limited to mass spectrometry, nuclear magnetic resonance spectroscopy and infrared spectroscopy.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. One skilled in the art will be able to identify optimal reaction conditions for each transformation without undue experimentation.

While the following schemes often depict specific compounds; the reaction conditions are exemplary and can readily be adapted to other reactants. Alternative conditions also are well known. The reaction sequences in the following examples are not meant to limit the scope of the invention as set forth in the claims.

Examples of representative compounds encompassed by the present invention and within the scope of the invention are provided in the following Tables. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight.

TABLE I

| Cpd. No. | STRUCTURE | mw | ms | mp | HIV-RT $IC_{50}$ RT |
|---|---|---|---|---|---|
| I-1 | [structure: Br-phenyl-O-phenyl(Cl)-CH2-dihydrotriazinone with Me] | 408.68 | 408 | — | 4.52 |

TABLE I-continued

| Cpd. No. | STRUCTURE | mw | ms | mp | HIV-RT IC$_{50}$ RT |
|---|---|---|---|---|---|
| I-2 | 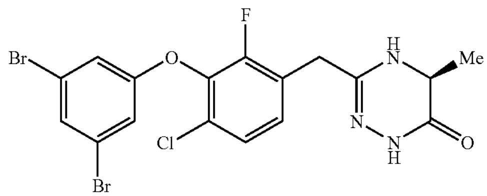 | 505.57 | 505 (M + H) | 88.0-91.5 | 0.1651 |
| I-3 | 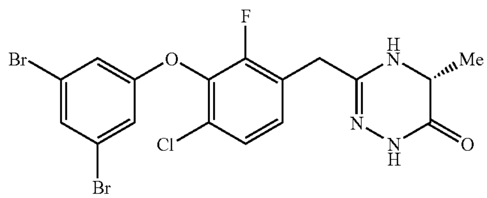 | 505.57 | 505 (M + H) | 75.2-79.1 | 0.0107 |
| I-4 | 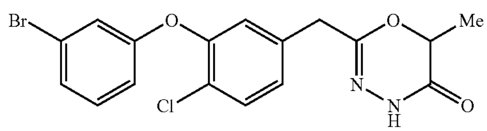 | 409.67 | 409 (M)+ | | 0.0515 |
| I-5 | 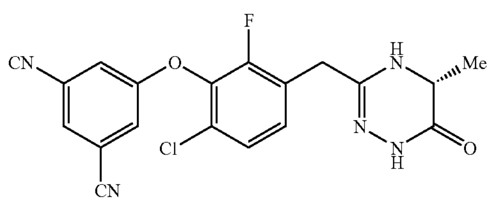 | 397.8 | 398 (M + H) | 81.5-100.0 | 0.0318 |
| I-6 | 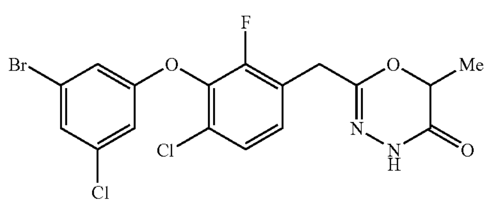 | 462.1 | 463 (M + H) | 163.3-155.4 | 0.0247 |
| I-7 | 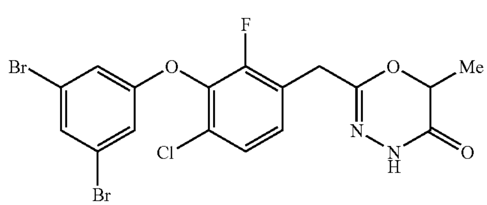 | 506.55 | 507 (M + H) | 174.2-176.1 | 0.0245 |
| I-8 | 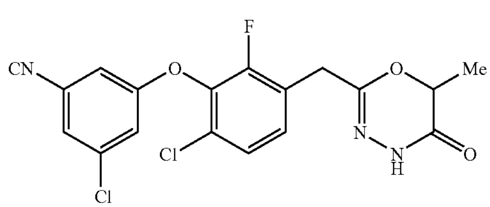 | 408.22 | 408 (M + H) | 166.6-167.1 | 0.0136 |

TABLE I-continued

| Cpd. No. | STRUCTURE | mw | ms | mp | HIV-RT IC$_{50}$ RT |
|---|---|---|---|---|---|
| I-9 | 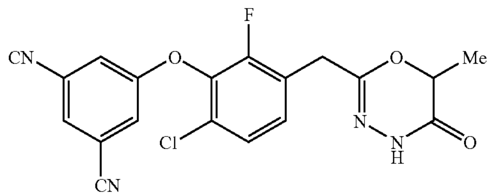 | 398.78 | 399 (M + H) | 60.9-67.7 | 0.0403 |
| I-10 | 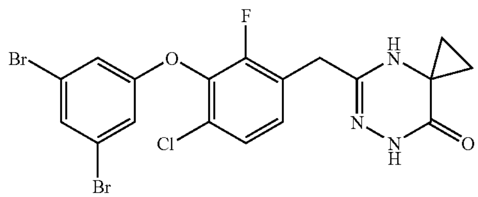 | 517.58 | 515 (ESI) | 90.0-95.0 | 0.066 |
| I-11 | 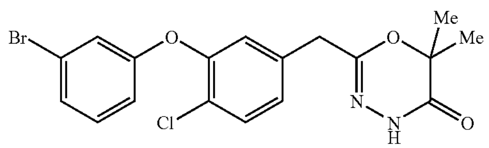 | 423.69 | 422 (ESI) | — | >10 |
| I-12 | 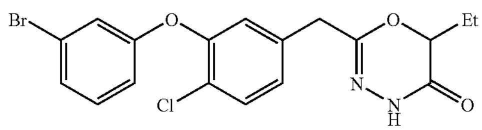 | 423.69 | 422 (ESI) | — | 0.2125 |
| I-13 | 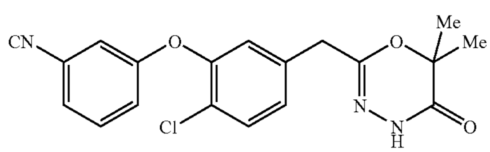 | 369.81 | 369 (ESI) | 94.1-95.3 | 9.49 |
| I-14 | 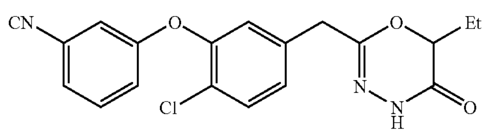 | 369.81 | 369 | 106.1-168.8 | 0.1275 |
| I-15 | 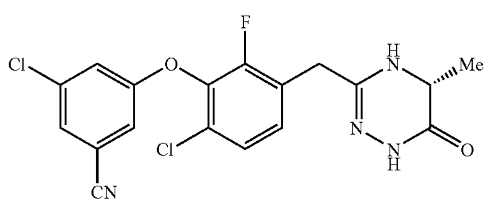 | 407.23 | 406 (M − H) | 158.6-159.9 | 0.0111 |
| I-16 | 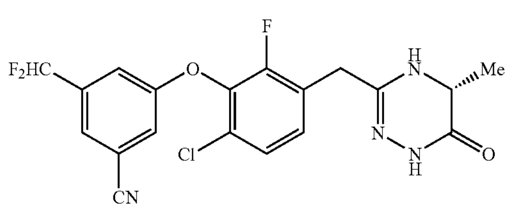 | 422.79 | 422 | | 0.0153 |

TABLE I-continued

| Cpd. No. | STRUCTURE | mw | ms | mp | HIV-RT IC$_{50}$ RT |
|---|---|---|---|---|---|
| I-17 | 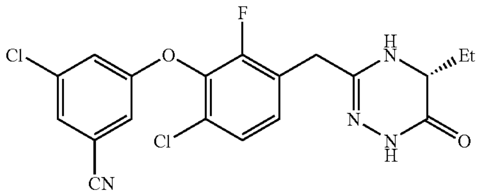 | 421.26 | 420 (M − H) | | 0.013 |
| I-18 | 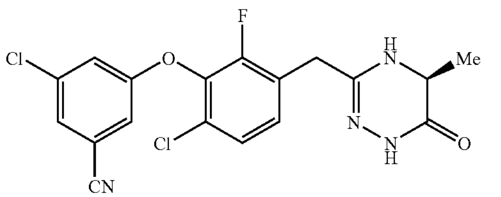 | 407.23 | 406 (M − H) | | 0.0119 |
| I-19 | 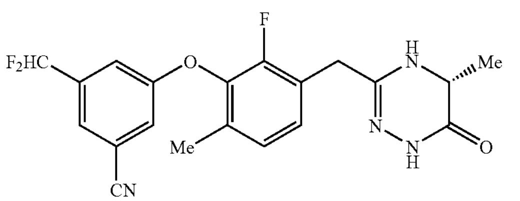 | 402.37 | 402 | | 0.018 |
| I-20 | 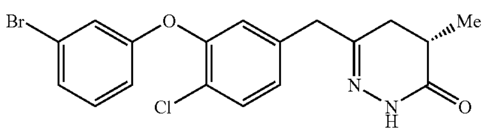 | 407.69 | 406 | — | 0.0654 |
| I-21 | 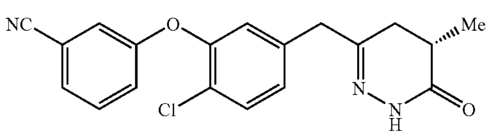 | 353.81 | 353 | — | 0.0469 |
| I-22 | 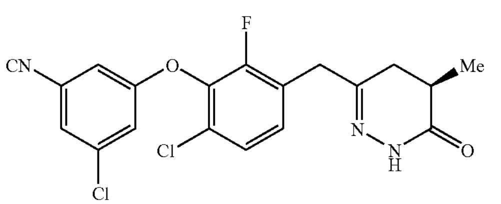 | 406.24 | 406 | 156.5-157.2 | 0.0177 |
| I-23 | 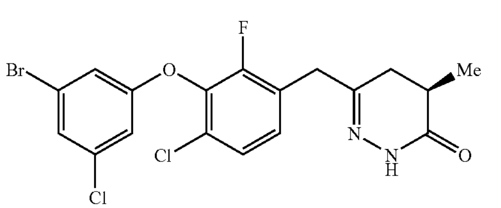 | 460.13 | 458 | 148.2-151.0 | 0.0143 |
| I-24 | 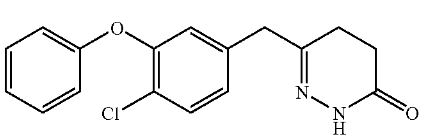 | 314.82 | 315 (M + H) | — | 2.63 |

TABLE I-continued
| Cpd. No. | STRUCTURE | mw | ms | mp | HIV-RT IC$_{50}$ RT |
|---|---|---|---|---|---|
| I-25 | 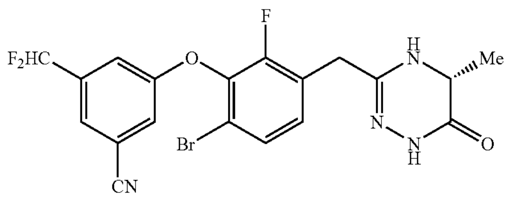 | 467.24 | 466 (M − H) | 231.5-233 | 0.0117 |
| I-26 | 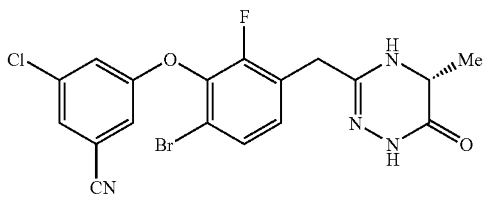 | 451.68 | 450 (M − H) | 178.2-179 | 0.0066 |
| I-27 | 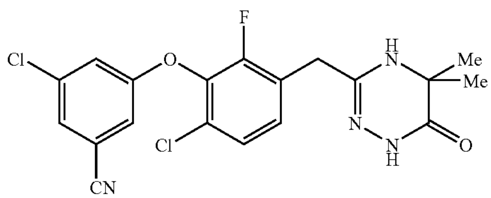 | 421.26 | 420 (M − H) | — | 7.07 |
| I-28 | 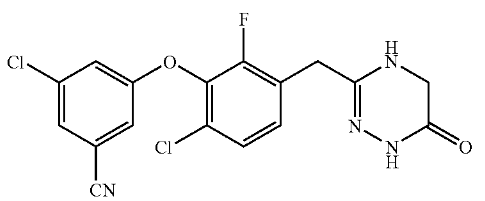 | 393.2 | 392 (M − H) | 177.6-178 | 0.1427 |
| I-29 | 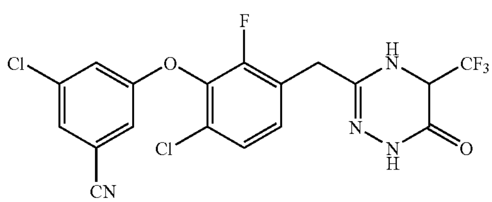 | 461.2 | 460 (M − H) | | 0.0269 |
| I-30 | 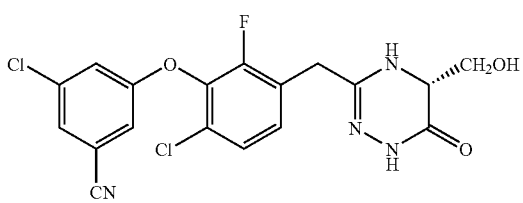 | 423.23 | 422 (M − H) | 112.5-114 | 0.4185 |
TABLE II
| Cpd. No. | STRUCTURE | mw | ms | mp | HIV-RT IC$_{50}$ RT |
|---|---|---|---|---|---|
| II-1 | 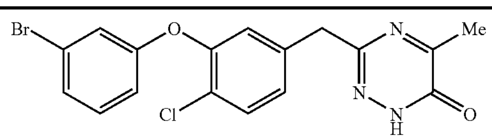 | 406.67 | 407 | | 0.3306 |

TABLE II-continued

| Cpd. No. | STRUCTURE | mw | ms | mp | HIV-RT IC$_{50}$ RT |
|---|---|---|---|---|---|
| II-2 | NC-C6H4-O-C6H3(Cl)-CH2-triazinone-Me | 352.78 | | 145.3-145.8 | 0.2062 |
| II-3 | Br-C6H4-O-C6H3(Cl)-CH2-triazinone-Ph | 468.74 | | 59.8-63.9 | 0.346 |
| II-4 | (3,5-Br2)C6H3-O-C6H2(F)(Cl)-CH2-triazinone-Me | 503.55 | 503 (M + H) | 180.9-183.3 | 0.1366 |
| II-5 | (3,5-(NC)2)C6H3-O-C6H2(F)(Cl)-CH2-triazinone-Me | 395.78 | 396 (M + H) | 194.7-197.4 | 0.4324 |
| II-6 | (3-Br-5-CN)C6H3-O-C6H2(F)(Cl)-CH2-triazinone-Me | 449.67 | 449 (M + H) | | 0.0325 |

3-Aralkyl-4,5-dihydro-1H-[1,2,4]triazin-6-ones 10 can be prepared by cyclization of α-acylaminoacids compounds 11 wherein X is O-alkyl (H. Neunhoeffer, "1,2,4-Triazines and their Benzo Derivatives" in *Comprehensive Heterocyclic Chemistry II*; A. J. Boulton, vol. Ed. Pergamon Press: Oxford, 1996, p. 561). Thus, compounds of the present invention can be

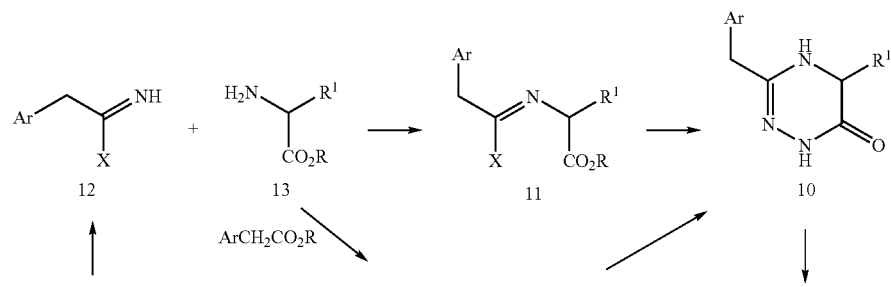

SCHEME 1

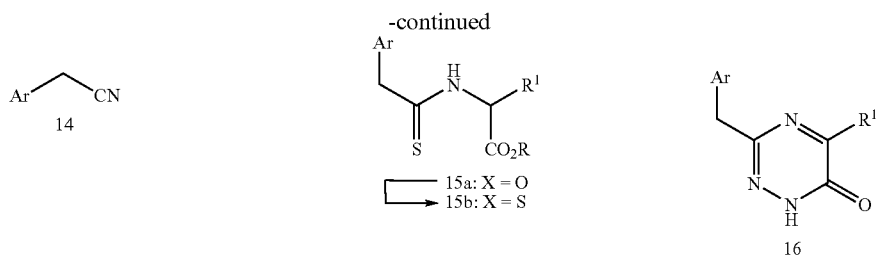

conveniently prepared by imine exchange of an alkyl imidate 12 (X=lower alkoxy) and a α-amino ester 13 which affords an (1-alkoxy-2-phenyl-ethylideneamino)-acetic acid ester 11. The availability of α-amino esters with diverse substitution on the α-carbon affords a convenient method to introduce a variety of substitutents onto the triazinone ring. Contacting imine 11 with hydrazine results in the addition to the imidate carbon and cyclization at the ester carbon to afford the triazinone 10. (A. Kjaer, *Acta Chem. Scand.* 1953 7:1024-29) The requisite imidate esters are prepared by contacting the corresponding nitrile with an alcohol in the presence of acid. Alternatively, (2-aryl-thioacetylamino)-acetic acid esters 15b can be directly cyclized to 1o. (T. P. Andersen et al. *Tetrahedron* 1983 39(20):3419-3427)

3-Benzyl-1H-[1,2,4]triazin-6-ones 16 are readily prepared by contacting the corresponding 4,5-dihydro-1H-[1,2,4]triazin-6-ones 10 with a mild oxidant, e.g. sodium hypochlorite.

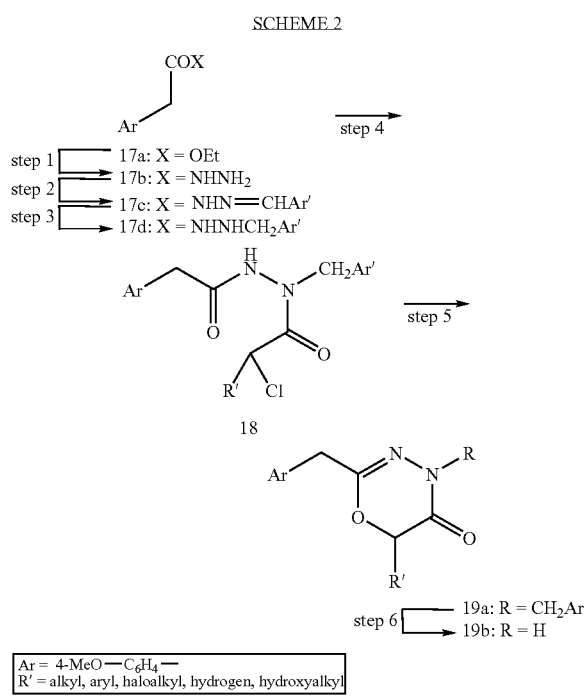

2-Aralkyl-4H-[1,3,4]oxadiazin-5-ones 19b can be prepared by intra-molecular cyclization of an N-(2-haloalkanoyl)-N-aralkyl-N' arylacetyl-hydrazide 18 and subsequent removal of the aralkyl substituent on the nitrogen atom. The 4-methoxybenzyl group was removed by treating 19a with AlCl₃ to afford 19b.

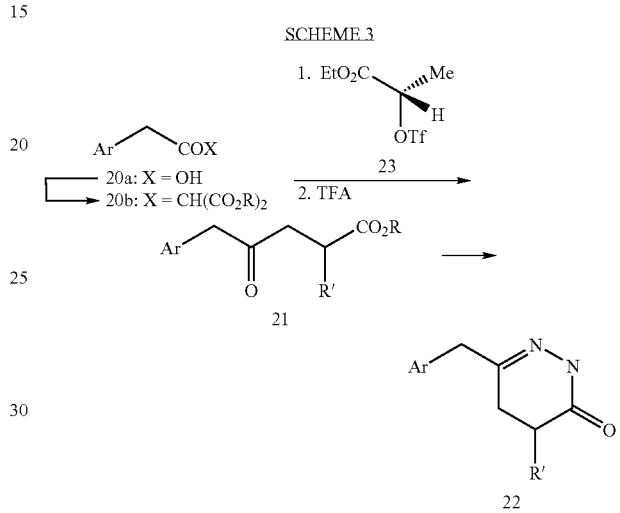

6-Aralkyl-4,5-dihydro-2H-pyridazin-3-ones 22 are readily prepared from γ-keto-esters 21 which are well known in the art and easily prepared. In the present instance, the requisite γ-keto-esters were prepared by stepwise addition of a malonate ester followed by alkylation of the active malonate carbon with an acetic acid derivative 23. Exposure of the γ-keto-ester obtained from decarboxylation of the malonate to hydrazine results in efficient cyclization to afford 22.

The requisite precursors for the routes depicted in SCHEMES 1-3 are 3-phenoxy-phenyl acetic esters (17a or the corresponding carboxylic acid) or 3-phenoxy-phenyl acetonitriles 14. Both the phenoxy substituent and the phenyl ring with a pendant acetic acid or acetonitrile are optionally substituted as described in the claims and the symbols R, R', R¹ and Ar are intended to generalize the SCHEME to the extent that these positions are defined in the claims and specification.

The preparation of diaryl ethers has been reviewed (J. S. Sawyer, "Recent Advances in Diaryl Ether Synthesis", *Tetrahedron* 2000 56:5045-5065). Introduction of the (hetero) aryloxy ether can often be accomplished by direct $S_NAr$ displacement reaction on an aromatic ring substituted with a leaving group and electronegative substituents. Fluoroaromatic compounds with electronegative substituents are known to be sensitive to nucleophilic attack by soft nucleophiles. Fluorine substituents are generally significantly more labile than other halogen substituents. While hard nucleophiles like water and hydroxide fail to displace fluoride, soft nucleophiles like phenols, imidazoles, amnines, thiols and some amides undergo facile displacement reactions even at room temperature (D. Boger et al., *Biorg. Med. Chem. Lett.* 2000 10:1471-75; F. Terrier *Nucleophilic Aromatic Displacement: The Influence of the Nitro Group* VCH Publishers, New York, N.Y. 1991). Phenols typified by 28 and 31a can be treated with appropriately substituted aryl fluorine compounds to produce diaryl ethers (infra).

Aryl ethers also can be efficiently prepared by Cu(OAc)$_2$ catalyzed condensation of substituted benzene boronic acids and phenols (D. A. Evans et al., *Tetrahedron Lett.* 1998 39:2937-2940 and D. M. T. Chan et al., *Tetrahedron Lett.* 1998 39:2933-2936). This protocol can also be adapted to phenols such as 28 and 31a. Benzene boronic acids with a variety of other substituents are widely available.

Alternatively, variations of the Ullmann diaryl ether synthesis with Cu(I) salts (J.-F. Marcoux et al., *J. Am. Chem. Soc.* 1997 119:10539-540; E. Buck et al, *Org. Lett.* 2002 4(9): 1623-1626) or palladium-catalyzed coupling procedures also has been reported (G. Mann et al., *J Am. Chem. Soc.,* 1999 121:3224-3225) have been described. One skilled in the art will appreciate that optimal procedure will vary depending on the nature and position of substituents on the aryl rings to be coupled and useful conditions for the coupling can by identified without undue experimentation.

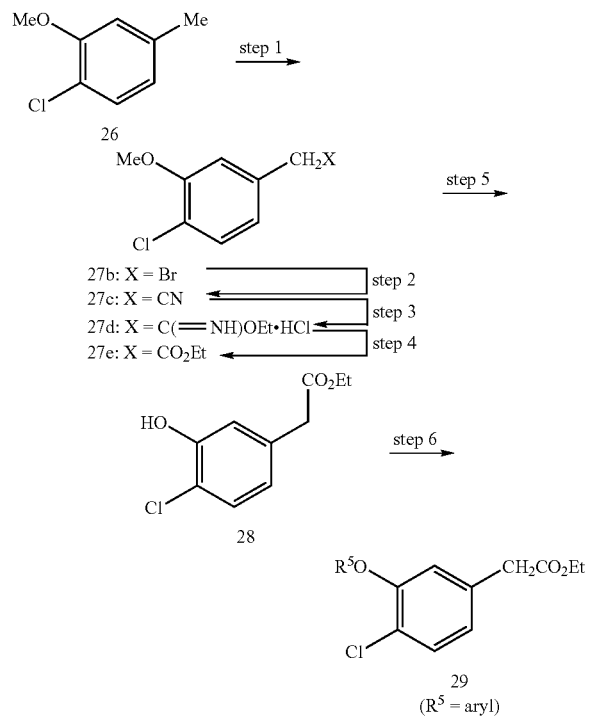

Many useful variously substituted 3-hydroxy phenylacetic acids (or precursors thereof) are commercially available and can be used to prepared compounds of the present invention. An alternative route utilizing optionally substituted 3-alkoxy-toluene compounds to elaborate the acetic acid (or acetonitrile) side chain has been used. Ethyl 4-chloro-3-hydroxy-phenylacetate (28) was prepared from 1-chloro-2-methoxy-4-methyl-benzene (26) by benzylic bromination (step 1) and displacement of the bromine atom with sodium cyanide (step 2). Hydrolysis of the nitrile (steps 3 and 4) and demethylation of the ether under standard conditions affords 28. BBr$_3$ or LiI/syn collidine mediated demethylation are effective techniques for conversion of methyl ethers to the corresponding phenols. Incorporation of the aryl ether is achieved by one of the methods described previously. Displacement of an aryl fluoride has proven effective if an appropriate precursor is available. Alternatively coupling of the phenol and an aryl boronic acid will afford a diaryl ether.

4-Chloro-2-fluoro-3-phenoxy-phenylacetic acid compounds (SCHEME 5) can prepared by starting from 1-chloro-3-fluoro-2-methoxy4-methylbenzene (30a) utilizing a sequence comprising benzylic bromination with NBS and AIBN, cyanide displacement, hydrolysis of the nitrile and esterification of the carboxylic acid to afford 30e in a reaction sequence analogous to that described in SCHEME 4

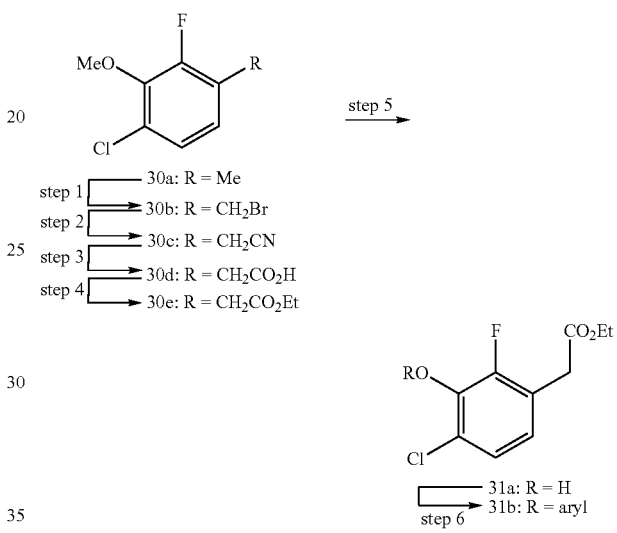

Alternatively, the synthesis of 2-fluoro substituted compounds was accomplished by exploiting the facile displacement of fluorine atoms from fluoroaromatic compounds. Treatment of 1,2,3-trifluoro4-nitro-benzene (32) with an alkali metal phenolate results in displacement of the 3-fluoro group with good regioselectivity to afford 33a (SCHEME 6). Treatment of 33a with carbanion formed by deprotonation of tert-butyl ethyl malonate results in the regioselective introduction of a malonic ester 33b which is subjected to acid-catalyzed hydrolysis of the tert-butyl ester and decarboxylation to afford 33c. In analogous fashion, replacement of tert-butyl ethyl malonate with tert-butyl cyano-acetate affords the acetonitrile 33d after hydrolysis and decarboxylation. After introduction of the phenoxy and acetic acid (or acetontrile) moieties, the nitro group is readily converted to other substituents at the 4-position. Reduction of the nitro substituent afforded 34a which can be subjected to Sandmeyer conditions to introduce a bromo 34b or chloro 34e substituent. The bromo substituent could be further reacted with a dialkyl zinc (the Negishi coupling) to afford 4-alkyl-3-aryloxy-2-fluoro-phenylacetic acid compounds exemplified by 34c and 34d.

The Negishi coupling of organozinc halides or dialkylzinc with haloarenes and aryl triflates is an effective means for attachment of an alkyl group to an arene. The reaction is catalyzed by palladium Pd(0) and palladium is preferably ligated to a bidentate ligand including Pd(dppf)Cl$_2$ and Pd(dppe)Cl$_2$. (J. M. Herbert *Tetrahedron Lett.* 2004 45:817-819) Typically the reaction is run an inert aprotic solvent and common ethereal solvents include dioxane, DME and THF are suitable. The reaction is commonly run at elevated temperature.

SCHEME 6

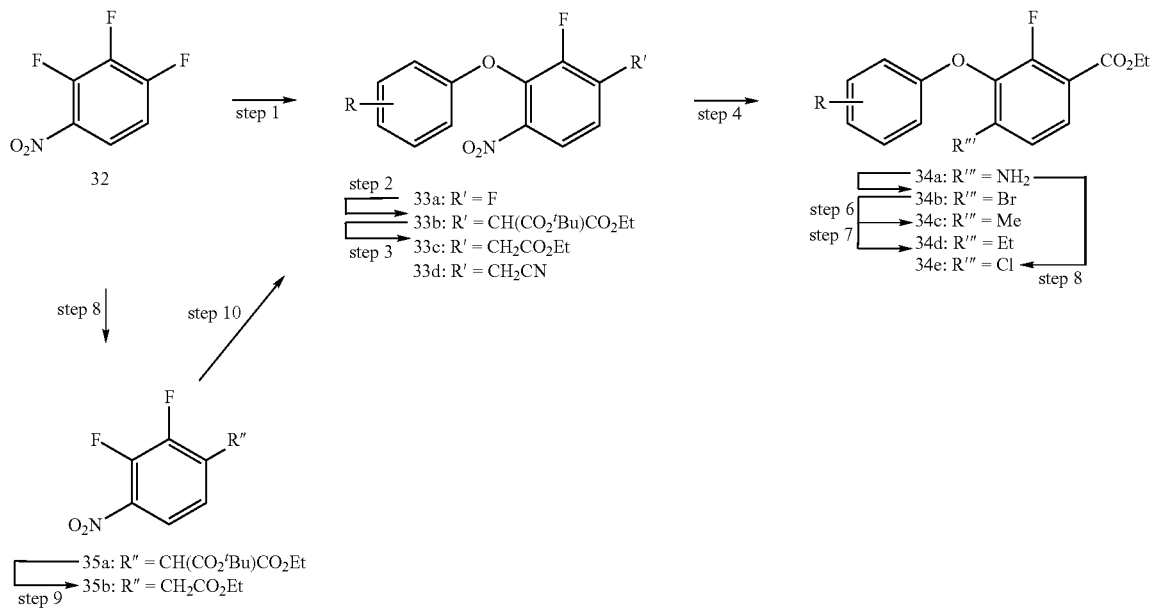

Alternatively, the reaction of the tert-butyl ethyl malonate or tert-butyl cyano-acetate affords a regioisomeric mixture of adducts in which displacement of the fluorine at the 1-position 35a (or the corresponding acetonitrile) predominates. The ratio of 1:3 isomers is approximately 2:1 and the compounds can be separated by silica chromatography. Hydrolysis and decarboxylation of 35a affords the phenylacetic acid 35b which is an effective substrate for introduction of an aryl ether and Sandmeyer-type chemistry.

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration.

The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. N-acylsulfonamides have an acidic proton which can be abstracted to form a salt with an organic or inorganic cation.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in Remington: *The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another non-nucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other animals. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

EXAMPLE 1

(R)-3-[4-Chloro-3-(3,5-dibromo-phenoxy)-2-fluoro-benzyl]-5-methyl-4,5-dihydro-1H-[1,2,4]triazin-6-one (I-3) and 5-[6-Chloro-2-fluoro-3-((R)-5-methyl-6-oxo-1,4,5,6-tetrahydro-[1,2,4]triazin-3-ylmethyl)-phenoxy]-isophthalonitrile (I-5)

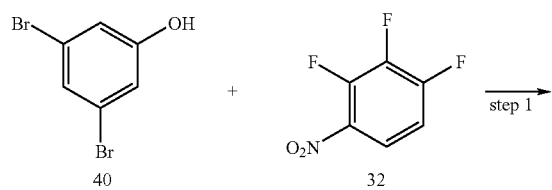

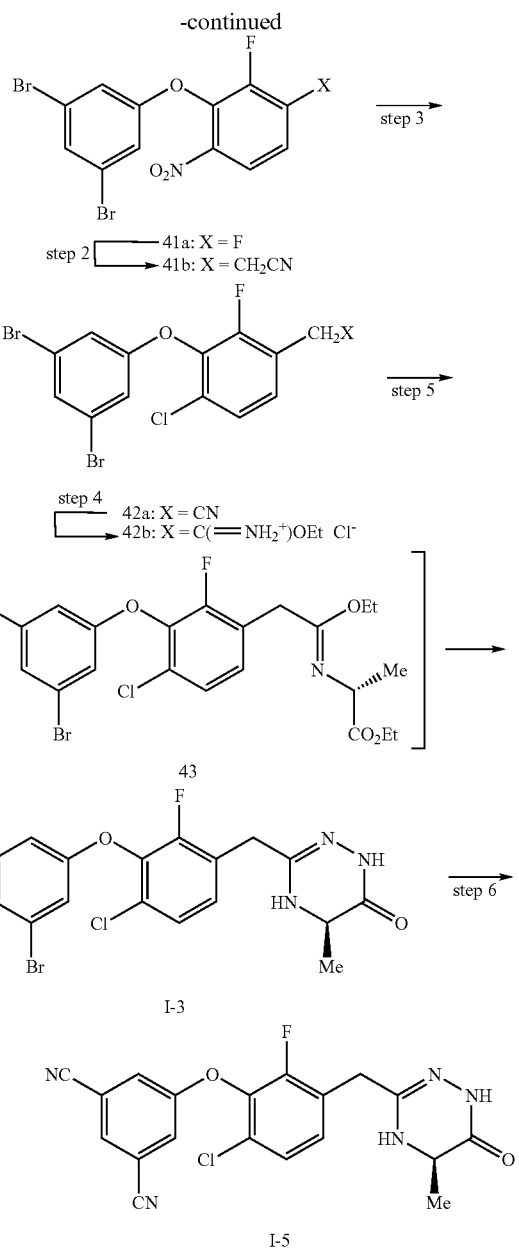

step 1—Sodium tert-butoxide (0.76 g, 1 equiv) was added in one portion to a solution of 3,5-dibromophenol (40, 2.0 g, 7.9 mmol) in dry THF (16 mL). The solution was cooled to 0° C., and 2,3,4-trifluoronitrobenzene (32, 0.91 mL, 1 equiv) was added dropwise via syringe. The solution was warmed to RT, stirred overnight, and poured into water. The mixture was extracted with EtOAc, and the combined organics were washed with water, brine, and dried over magnesium sulfate. Filtration and evaporation afforded 3.26 g (100%) of 41a as an oil that slowly crystallized.

step 2—Anhydrous $CS_2CO_3$ (10.5 g, 1.2 equiv) was added to a solution of 41a (11.0 g, 27 mmol) and tert-butyl cyanoacetate (4.2 g, 1.1 equiv) in dry DMF (110 mL). The solution was heated to 90° C. for 3 h, cooled to RT, and poured into a solution of concentrated ammonium hydroxide. The aqueous layer was extracted with EtOAc/hexanes (1:1), and the combined organics were washed with water and brine. Evaporation of the volatile materials afforded ca. 15 g of a red oil. The oil was dissolved in dichloroethane (135 mL), and TFA (6.8 mL) was added. The solution was heated to reflux for 3 h and cooled to RT. The volatile materials were removed, and the remaining oil was partitioned between DCM and water. The aqueous layer was extracted with DCM, and the combined extracts were washed with $NaHCO_3$ and brine. The crude product was purified by $SiO_2$ chromatography eluting with a EtOAc/hexane gradient (20 to 60% EtOAc) to afford 9.0 g (84%) of 41b as an oil.

step 3—A suspension of 41b (0.80 g, 1.8 mmol), iron powder (0.44 g, 4.2 equiv), and $NH_4Cl$ (0.42 g, 4.2 equiv) in EtOH (3.7 mL) and $H_2O$ (3.7 mL) was heated to 90° C. for 12 h. The solution was cooled to RT and filtered through CELITE® and the pad was washed with EtOAc. The combined organics were washed with water, brine, and dried ($MgSO_4$). Evaporation of the volatile materials afforded 0.68 g (91%) of the corresponding aniline as a brown oil.

tert-Butyl nitrite (3.72 mL, 2 equiv) was added to a suspension of $CuCl_2$ (4.21 g, 2 equiv) in dry MeCN (39 mL) at 60° C. maintained under an Ar atmosphere. A solution of the aniline (6.26 g, 15.7 mmol) in MeCN (39 mL) was added dropwise over 45 min. The solution was stirred at 60° C. for an additional 10 min, and then cooled to 0° C. The reaction was quenched with 10% HCl (5 mL). Water was added to the reaction mixture, and the solution was extracted with EtOAc. The combined organics were washed with water, brine, and dried ($MgSO_4$). Evaporation of the volatile materials and purification by $SiO_2$ chromatography eluting with a EtOAc/hexane gradient (5 to 20% EtOAc) afforded 2.7 g (40%) of 42a as a white solid.

step 4—An oven-dried round-bottom flask was charged with nitrile 42a (2.68 g, 6.4 mmol) and the flask was purged with $N_2$. To the flask was added anhydrous toluene (18 mL) and anhydrous ethanol (0.432 mL, 7.66 mmol). The solution was cooled to 0° C. and HCl gas was bubbled through the solution for 15 min while flushing the flask with $N_2$. The solution was sealed and stored at −10° C. over 36 h. During this time, the desired product precipitated out of solution. The white solid was collected and washed with anhydrous ethyl ether and dried under high vacuum to obtain 2.77 g (84%) of 42b as a white solid that was used without any further purification.

step 5—An oven-dried round-bottom flask was charged with 42b (100 mg, 0.2 mmol) and ethyl L-alanine hydrochloride (28 mg, 0.2 mmol). The mixture was purged with argon and suspended in anhydrous DCM (1 mL). To the suspension was added TEA (30.5 µL, 0.22 mmol) and the mixture was stirred at 40° C. for 12 h. The solution was then diluted with DCM (15 mL) and washed with water (5 mL) and brine (5 mL). The organic layer was concentrated in vacuo and the unstable imine 43 was immediately dissolved in EtOH (1 mL). Hydrazine monohydrate (85% in water, 28 µL, 0.2 mmol) was added and the mixture heated at reflux under a $N_2$ atmosphere for 2 h. The reaction mixture was cooled, diluted with EtOAc and washed sequentially with water (15 mL) and brine (5 mL). The organic layer was dried ($MgSO_4$), filtered and concentrated in vacuo. The crude product was purified by $SiO_2$ column chromatography eluting with a DCM/MeOH gradient to afford 69 mg (68%) of I-3 as a white foam.

step 6—An oven-dried round-bottom was charged the I-3 (154 mg, 0.30 mmol), $Zn(CN)_2$ (50 mg, 0.43 mmol), and $Pd(PPh_3)_4$ (88 mg, 76 µmol). The mixture was purged with argon then suspended in anhydrous DMF (1.5 mL). The mixture was heated at 80° C. under argon atmosphere for 2 h. The reaction mixture was cooled to RT and diluted with 1:1 hexanes/EtOAc (25 mL) and washed with water (10 mL). The organic phase was washed with brine (5 mL), dried ($MgSO_4$), filtered and concentrated in vacuo. The crude product was purified by $SiO_2$ chromatography eluting with a DCM/MeOH gradient to afford 110 mg (91%) of I-5 as a white solid.

(S)-3-[4-Chloro-3-(3,5-dibromo-phenoxy)-2-fluoro-benzyl]-5-methyl4,5-dihydro-1H-[1,2,4]triazin-6-one (I-2) was prepared by the procedure in Example 1 except in step 5 the HCl salt L-alanine ethyl ester was replaced with the HCl salt of D-alanine ethyl ester.

3-Chloro-5-[6-chloro-2-fluoro-3-((R)-5-methyl-6-oxo-1, 4,5,6-tetrahydro-[1,2,4]triazin-3-ylmethyl)-phenoxy]-benzonitrile (I-15) was prepared by the procedure in Example 1 except in step 1,3,5-dibromophenol was replaced by 3-bromo-5-chlorophenol to afford 2-(3-bromo-5-chloro-phenoxy)-3,4-difluoro-1-nitro-benzene which was converted to I-15 as described in this example.

3-Chloro-5-[6-chloro-2-fluoro-3-(5-methyl-6-oxo-1,4,5, 6-tetrahydro-[1,2,4]triazin-3-ylmethyl)-phenoxy]-benzonitrile (I-18) was prepared in the same manner as I-15 except in step 5 the HCl salt L-alanine ethyl ester was replaced with the HCl salt of D-alanine ethyl ester.

3-Chloro-5-[6-chloro-3-((R)-5-ethyl-6-oxo-1,4,5,6-tetrahydro-[1,2,4]triazin-3-ylmethyl)-2 -fluoro-phenoxy]-benzonitrile (I-17) was prepared by the procedure in Example 1 except in step 5 L-alanine ethyl ester HCl was replaced with ethyl L-2-aminobutyrate HCl.

EXAMPLE 2

5-[4-Chloro-3-(3,5-dibromo-phenoxy)-2-fluoro-benzyl]-4,6,7-triaza-spiro[2.5]oct-5-en-8-one (I-10)

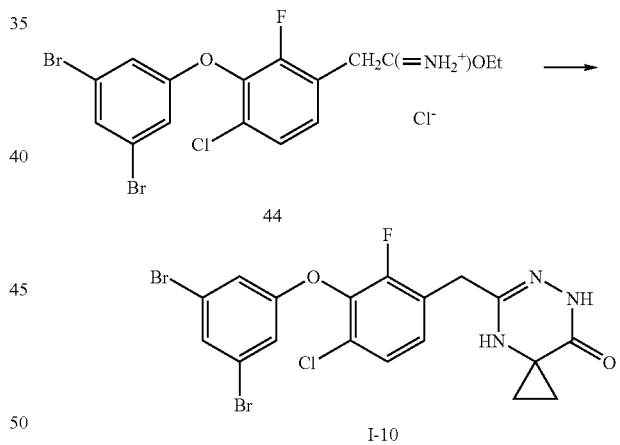

The imidate 44 (0.145 g, 0.29 mmol) and 1-amino-cyclopropane carboxylic acid ethyl ester (0.048 g, 0.29 mmol) were suspended in DCM (1.1 mL) and maintained under a nitrogen atmosphere. TEA (44 µL, 1.1 equiv) was added dropwise, and the mixture was stirred at 35° C. After 5 h, the solution was cooled to RT, diluted with DCM, washed with brine, and dried ($Na_2SO_4$). The volatile materials were evaporated and the crude imidate product was used without further purification. The imidate was dissolved in EtOH (1.4 mL), and hydrazine (54 µL, 4 equiv) was added. The solution was refluxed for 2 h, cooled to RT, and diluted with EtOAc. The organic layer was washed with brine, dried ($MgSO_4$) and concentrated. The crude product was purified by $SiO_2$ chromatography eluting with an EtOAc/hexane gradient (20% to 80% EtOAc) to afford 0.12 g (81%) of I-10 as a white foam.

EXAMPLE 3

3-[6-Chloro-2-fluoro-3-((R)-5-methyl-6-oxo-1,4,5,6-tetrahydro-[1,2,4]triazin-3-ylmethyl)-phenoxy]-5-difluoromethyl-benzonitrile (I-16)

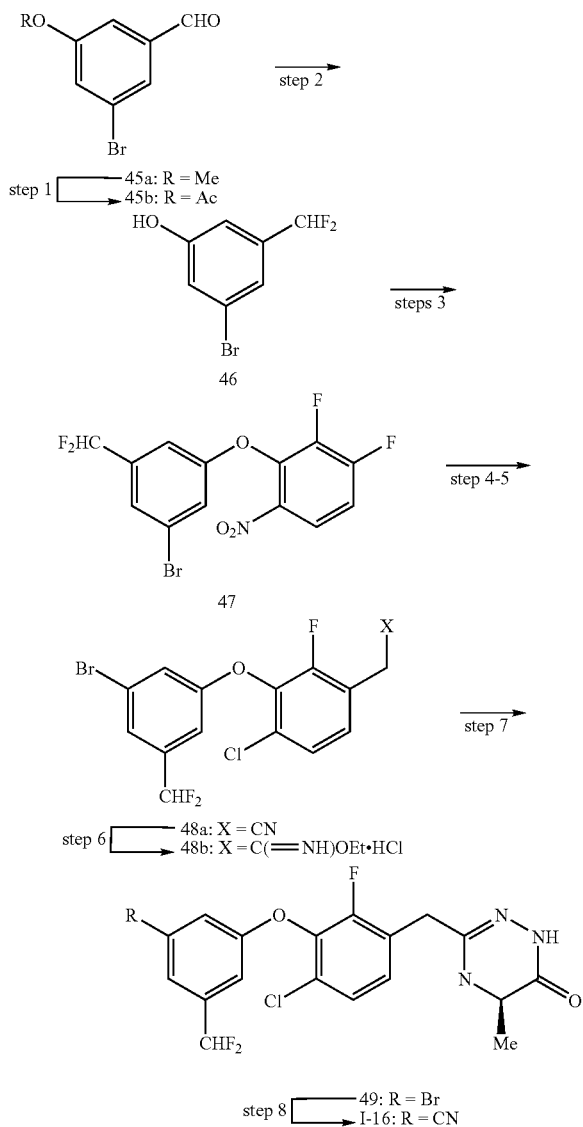

step 1—A solution of BBr₃ (29.1 mL of a 1.0 M solution in DCM, 29.1 mmol) was added slowly to a solution of 45a (2.5 g, 11.62 mmol) in anhydrous DCM (25 mL) maintained under N₂ at −78° C. The orange solution was warmed to RT, stirred for 2 h, and poured onto ice. The mixture was extracted with DCM (100 mL), and the organic layer was washed with H₂O (50 mL) and brine (50 mL). The solvents were evaporated, and the remaining oil was purified by flash chromatography on SiO₂ eluting with an EtOAc/hexane gradient (0% to 20% EtOAc) to provide the desired phenol. To a solution of this phenol in pyridine (10 mL) under argon was slowly added acetic anhydride (0.6 mL, 6.33 mmol). After 2 h, the volatile materials were removed to provide 3-bromo-5-formyl-phenyl acetate (45b, 1.02 g, 40%).

step 2—DAST (1.02 mL, 7.69 mmol) was added to a solution of the 3-bromo-5-formyl-phenyl acetate (45b, 1.1 g, 4.52 mmol) in DCM (5 mL) under nitrogen contained in a NALGENE® bottle. EtOH (0.013 mL, 0.23 mmol) was added, and the mixture was stirred for 16 h. The reaction mixture was then added slowly to an aqueous solution of saturated NaHCO₃. After the bubbling was finished, DCM (50 mL) was added and the layers were separated. The organic layer was washed with brine (30 mL) and dried with anhydrous MgSO₄. The solvent was removed to provide a yellow oil that was placed in a mixture of THF (15 mL) and H₂O (4 mL). LiOH monohydrate (474 mg, 11.3 mmol) was added, and the reaction mixture was stirred at RT for 2 h. The solution was then added dropwise to 5% aqueous HCl (50 mL), and the mixture was extracted with EtOAc (3×30 mL). The combined organic fractions were washed with brine (30 mL), and dried (MgSO₄). Evaporation of the volatile materials gave an oil that was purified by flash chromatography on silica gel (0% to 25% EtOAc/hexanes) to provide 800 mg (79%) of 3-bromo-5-difluoromethylphenol (46).

steps 3-5—Sequential condensation of 46 with 2,3,4-trifluoro-nitro-benzene and addition of tert-butyl cyano acetate was carried out as described in steps 1 and 2 of example 1. Conversion of the nitro group to a chloride was carried out as described in step 3 of example 1 which afforded 48a.

step 6—HCl gas is bubbled into a cooled solution (5° C.) containing 48a (1.25 g, 3.20 mmol), EtOH (7 mL) and toluene (30 mL) for a 1 h. The resulting solution was evaporated to dryness and the residue triturated with Et₂O to afford 0.82 g (54%) of 48b.

step 7—TEA (0.265 mL, 1.91 mmol) was added to a mixture of 48b (0.82 g, 1.73 mmol), D-alanine methyl ester hydrochloride (0.97 g, 6.93 mmol) and DCM (20 mL). After stirring at RT for 2 h the reaction mixture is quenched by the addition of water. The organic phase was separated, dried (MgSO₄) and evaporated. The residue is dissolved in EtOH (20 mL) and 80% hydrazine hydrate (4.08 mL, 69.32 mmol) was added. The reaction mixture was stirred at 90° C. for 14 h, then cooled and evaporated in vacuo. The residue was dissolved in EtOAc, washed with brine, dried (MgSO₄) and evaporated to afford 0.60 g (73%) of 49 as a foam.

step 8—A solution of 49 (0.60 g, 1.26 mmol) in DMF (2 mL) was added to a round-bottom flask containing Zn(CN)₂ (0.10 g, 0.88 mmol), P(0)(PPh₃)₄ (0.04 g, 0.25 mmol) in DMF (20 mL). The reaction was stirred at 90° C. under an atmosphere of argon for 48 h. The reaction mixture was cooled and evaporated to dryness. The crude residue was dissolved in EtOAc, washed with brine solution, dried (MgSO₄) and evaporated. The crude product was purified by SiO₂ chromatography eluting with a MeOH/DCM gradient (2% to 5% MeOH) to afford 0.15 g (28%) of I-16: mp 173.2-174.8° C.; ms (M+H)=423.

EXAMPLE 4

3-Difluoromethyl-5-[2-fluoro-6-methyl-3-((R)-5-methyl-6-oxo-1,4,5,6-tetrahydro-[1,2,4]triazin-3-ylmethyl)-phenoxy]-benzonitrile (I-19)

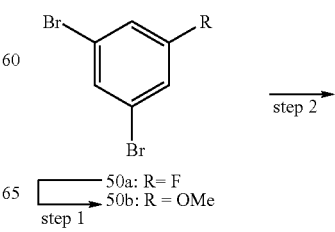

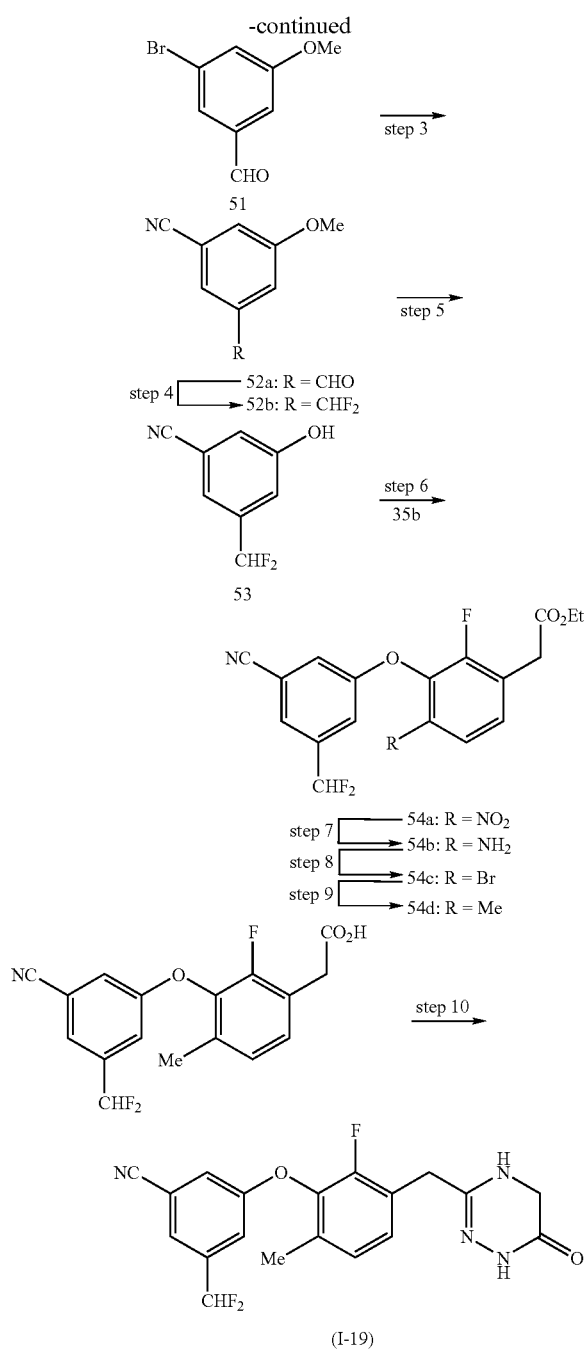

step 1—A solution of 50a, sodium methoxide (1 equivalent) and DMF were stirred overnight under an $N_2$ atmosphere at RT. The volatile solvents were removed in vacuo and the residue partitioned between $Et_2O$ and water. The organic phase was washed with 5% NaOH, water and brine, dried ($MgSO_4$), filtered and evaporated to afford 50b.

step 2—To a solution of 50b (60 g, 0.2256 mol) and anhydrous $Et_2O$ (1 L) cooled to −78° C. and maintained under an Ar atmosphere was added dropwise over 30 min n-BuLi (100 mL, 0.2482 mol, 2.5M in hexane). The yellow solution was stirred at −78° C. for 20 min. To the reaction mixture was added dropwise dry DMF (19 mL, 248.2 mmol) over 15 min and the reaction stirred at −78°C. for 10 min before the cooling bath was removed and the reaction allowed to warm to −30° C. over 30 min. The reaction vessel was placed in an ice-water bath and warmed to −10° C. The mixture was slowly added to an ice cold saturated aqueous $NH_4Cl$ solution (400 mL). The organic layer was separated and the aqueous phase thrice extracted with $Et_2O$. The combined extracts were washed with water, dried ($MgSO_4$), filtered and evaporated to afford an oil which solidified on standing. The crude product was purified by $SiO_2$ chromatography eluting with a hexane/EtOAc gradient (3 to 5% EtOAc) to afford 51.

step 3—Cyanation of 51 to afford 52a was carried out with $Zn(CN)_2$, $Pd(PPh_3)_4(0)$ and DMF as described in step 9 of example 3.

step 4—DAST (21.04 mL, 519 mmol) was added to a solution of 52a (15.1 g, 94 mmol) in DCM (100 mL) under nitrogen contained in a NALGENE® bottle. EtOH (0.013 mL, 0.23 mmol) was added and the mixture was stirred for 16 h. The reaction mixture was then added slowly to an aqueous solution of saturated $NaHCO_3$. After the bubbling was finished, DCM (50 mL) was added and the layers were separated. The organic layer was washed with brine (30 mL) and dried with anhydrous $MgSO_4$. The solvent was removed and the crude product was purified by two flash chromatographies on silica gel (0% to 10% EtOAc/hexanes) to afford 52b as a white solid.

step 5—The ether 52b is dissolved in glacial HOAc and 48% aqueous HBr and the solution is heated to 120° C. After 40 h, the volatiles are removed while heated to 80° C. and the residue is cooled to RT. The residue is partitioned between water (100 mL) and DCM (3×250 mL). The combined extracts are washed with $H_2O$ (50 mL), aqueous $NaHCO_3$ solution (2×50 mL), brine (50 mL), and ($MgSO_4$). The solvents are removed to afford 53.

step 6—An oven-dried round bottom flask was charged with 53 (9.07 g, 54 mmol) and dry THF (90 mL). The solution was cooled to 0° C. under nitrogen and sodium tert-butoxide (5.27 g, 55 mmol) was added slowly over several minutes. The clear yellow solution was stirred for 10 min at 0° C. A separate oven-dried round bottom flask was charged with 35b (13.148 g, 54 mmol) under nitrogen and dry THF (90 mL) was added. This solution was added to the sodium phenolate solution maintained at 0° C. slowly via syringe over 10 min. After stirring at RT overnight, the reaction was slowly poured into cold, saturated aqueous $KHSO_4$ (100 mL) and extracted twice with EtOAc (2×200 mL). The organic layers were combined and washed with brine (100 mL). The solution was dried ($MgSO_4$), filtered and concentrated in vacuo. The crude product was recrystallized by dissolving in hot $Et_2O$ (100 mL), adding hexane (50 mL) and storing in refrigerator for several hours. The precipitate was filtered to afford 13g of brown solid. The filtrate was concentrated and purified by $SiO_2$ chromatography eluting with EtOAc/hexanes to afford 10 g of 54a as a yellow solid. The product was combined with precipitate and the mixture recrystallized as described above to obtain 20g (94%) of 54a as white solid.

step 7—The bis-aryl ether 54a (16.36 g, 41.5 mmol), iron (9.732 g, 174 mmol), and $NH_4Cl$ (9.322 g, 174 mmol) were combined in a round bottom and suspended in EtOH (70 mL) and water (70 mL). The suspension was heated to reflux for 2.5 hrs, cooled to RT and filtered through CELITE®. The CELITE cake was washed repeatedly with EtOAc. The filtrate was combined and washed with brine, dried ($MgSO_4$), filtered and concentrated in vacuo. The crude material was purified by $SiO_2$ chromatography eluting with EtOAc/hexanes to afford 14.2 g (93%) of 54b as a white solid.

step 8—A 500 mL round bottom was charged the Cu(II) $Br_2$ (2.62 g, 11.7 mmol) and LiBr (3.052 g, 35.2 mmol). The mixture was purged with dry argon for 20 min. To this was added MeCN (150 mL) and stirred for 20 min at 50° C. until the solid particles were finely dispersed. To the suspension was added the tert-butyl nitrite and stirring continued for 5 min after which a solution of 54b (4.27 g, 11.72 mmol) and MeCN (40 mL) was added in a single portion. The resulting mixture was stirred at 70° C. for 1 h. The reaction mixture was cooled to 0° C. and quenched with 5% aqueous HBr (10 mL). The solution was diluted with EtOAc (200 mL) and washed with water (100 mL) and brine (50 mL). The organic layer was dried (MgSO$_4$), filtered and concentrated in vacuo. The crude material was purified by SiO$_2$ chromatography eluting with EtOAc/hexanes to obtain 2.6 g (52%) of 54c as a white solid.

step 9—An oven-dried round bottom flask was charged with the bromide 54c (3.0 g, 7 mmol) and Pd(dppf) CH$_2$Cl$_2$ (572 mg, 0.7 mmol). The mixture was purged with argon for 15 min. To the solid was added dry THF (35 mL), dimethylaminoethanol (0.14 mL, 1.4 mmol), and dimethyl zinc (1.1 M in toluene, 12.7 mL, 14 mmol). The resulting mixture was warmed to 65° C. for 10 min then cooled to 50° C. After 1 h, the reaction mixture was cooled to RT and added to saturated aqueous NH$_4$Cl (100 mL). The mixture was extracted with EtOAc (150 mL) and the organic layer was then washed with water (100 mL) and brine (50 mL). The organic layer was dried (MgSO$_4$), filtered and concentrated in vacuo. The crude product was purified by SiO$_2$ chromatography eluting with EtOAc/hexanes to afford 2.3 g (90%) of 54d as a white solid.

3-Difluoromethyl-5-[2-fluoro-6-methyl-3-((R)-5-methyl-6-oxo-1,4,5,6-tetrahydro-[1,2,4]triazin-3-ylmethyl)-phenoxy]-benzonitrile (I-19) is prepared from 54d by hydrolysis of 54b with LiOH dissolved in aqueous THF to afford 55 which is converted to I-19 by the procedure described in Example 9 except in step 1, L-alanine methyl ester is replaced by glycine methyl ester.

EXAMPLE 5

3-[4-Chloro-3-(3,5-dibromo-phenoxy)-2-fluoro-benzyl]-5-methyl-1H-[1,2,4]triazin-6-one (II-4) and 5-[6-chloro-2-fluoro-3-(5-methyl-6-oxo-1,6-dihydro-[1,2,4]triazin-3-ylmethyl)-phenoxy]-isophthalonitrile (II-5)

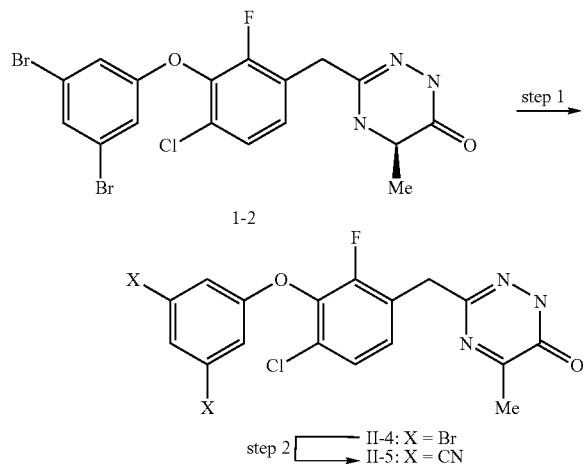

step 1—A round-bottom flask was charged with I-2 (Example 1, 253 mg, 0.5 mmol) and suspended in 10% aqueous sodium hydroxide (2 mL). The suspension was chilled to 0° C. and aqueous sodium hypochlorite (6 wt. %, 807 mg, 0.65 mmol) was added. The solution was warmed to RT and stirred for 1.5 h. The reaction was poured into a rapidly stirred solution of phosphate buffer (20 mL) adjusted to pH 7.0. The resulting mixture was extracted with EtOAc (100 mL) and the extract washed with brine (10 mL), dried (MgSO$_4$), filtered and concentrated in vacuo. The crude product was purified by SiO$_2$ column chromatography eluting with an EtOAc/hexane gradient to afford 150 mg (60%) of II-4 as a white solid.

step 2—An oven-dried round bottom flask was charged with II-4 (138 mg, 0.27 mmol), Zn(CN)$_2$ (48 mg, 0.41 mmol), and Pd(PPh$_3$)$_4$ (62 mg, 54 μmol). The mixture was purged with argon then suspended in anhydrous DMF (2.7 mL). The mixture was heated at 80° C. for 2 h while under an argon atmosphere. The reaction mixture was cooled to RT and diluted with 1:1 hexanes/EtOAc (25 mL) and thrice washed with water (10 mL). The organic phase was washed with brine (5 mL), dried (MgSO$_4$), filtered and concentrated in vacuo. The crude product was purified by SiO$_2$ chromatography eluting with a DCM/MeOH gradient followed by preparatory TLC on SiO$_2$ (MeOH/DCM) to yield 17 mg (15%) of II-5 as a white solid. 3-Bromo-5-[6-chloro-2-fluoro-3-(5-methyl-6-oxo-1,6-dihydro-[1,2,4]triazin-3-ylmethyl)-phenoxy]-benzonitrile (II-6) was isolated as a by-product from the reaction.

(S)-6-[3-(3-Bromo-5-chloro-phenoxy)4-chloro-2-fluoro-benzyl]-4-methyl-4,5-dihydro-2H-pyridazin-3-one (II-1) was prepared by the procedure described in step 1 of example 5 except I-2 was replaced by I-1.

3-[3-(3-Bromo-phenoxy)4-chloro-benzyl]-5-phenyl-1H-[1,2,4]triazin-6-one (II-3) was prepared by the procedure described in step 1 of example 5 except I-2 was replaced by 3-[3-(3-bromo-phenoxy)4-chloro-benzyl]-5-phenyl-4,5-dihydro-1H-[1,2,4]triazin-6-one which was prepared as described in example 1 except in step 5, alanine ethyl ester was replaced by 2-phenylglycine methyl ester.

3-[2-Chloro-5-(5-methyl-6-oxo-1,6-dihydro-[1,2,4]triazin-3-ylmethyl)-phenoxy]-benzonitrile (II-2) was prepared from II-1 by the procedure described in step 6 of example 1.

EXAMPLE 6

(S)-3-[3-(3-Bromophenoxy)-4-chloro-benzyl]-5-methyl4,5-dihydro-1H-[1,2,4]triazin-6-one (I-1)

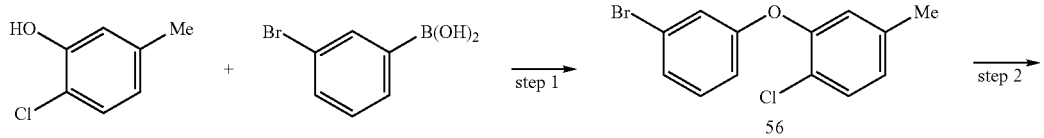

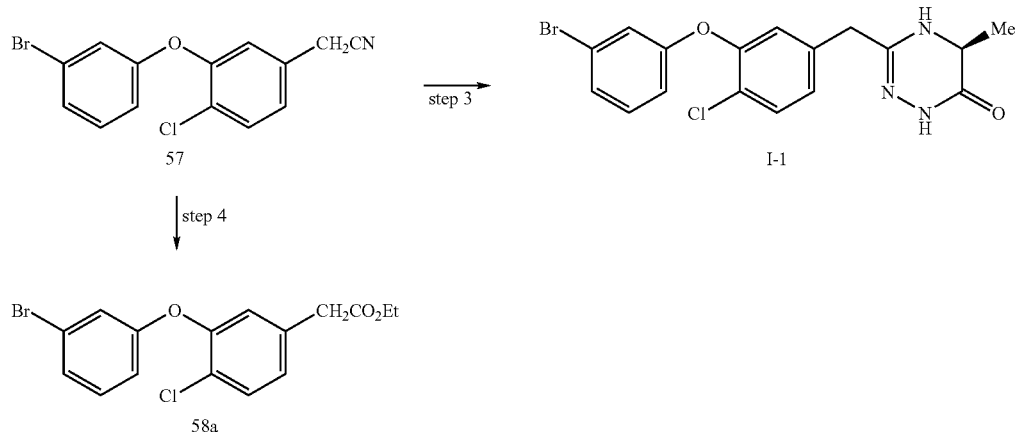

step 1—A mixture of 2-chloro-5-methyl-phenol (4.0 g, 28.06 mmol), 3-bromo-phenylboronic acid (11.3 g, 2.0 equiv), 4 Å molecular sieves (20 g) and Cu(OAc)$_2$ (5.6 g, 1 equiv) was suspended in anhydrous DCM (250 mL). TEA (19.6 mL, 5 equiv) was added, and air was briefly bubbled through the reaction mixture. After 24 h, the reaction mixture was filtered through CELITE® and the filtrate was washed sequentially with 10% HCl, water, and brine. Evaporation of the volatile materials provided 5.0 g (54%) of 56 as an oil that was purified by SiO$_2$ chromatography and eluting with hexanes.

step 2—A solution of 56 (4.78 g, 16.1 mmol), NBS (2.66 g, 0.95 equiv), AIBN (120 mgs, 0.075 equiv) and CCl$_4$ (70 mL) was heated to 80° C. An additional 80 mg of AIBN was added to the reaction mixture. After 3 h, the mixture was cooled and filtered through a pad of SiO$_2$ which was washed with DCM. Evaporation of the volatile materials afforded an oil that was dissolved in EtOH (80 mL) and MeCN (15 mL). Sodium cyanide (3.9 g, 5 equiv) was added to the reaction mixture, and the suspension was stirred for 16 h. The solution was filtered through SiO$_2$ eluting with EtOAc. The volatile materials were removed, and the remaining material was purified by SiO$_2$ chromatography eluting with an EtOAc/hexane gradient (0% to 25% EtOAc) to afford 3.56 g (69%) of 57.

step 3—(S)-3-[3-(3-Bromo-phenoxy)-4-chloro-benzyl]-5-methyl-4,5-dihydro-1H-[1,2,4]triazin-6-one (I-1) was prepared from 57 by the procedure in steps 4 and 5 of example 1.

step 4—To a solution of 57 (0.42 g, 1.3 mmol, anhydrous toluene (7 mL) maintained under an N$_2$ atmosphere was added EtOH (0.09 mL, 1.2 equiv) and HCl (g) was bubbled through the reaction mixture for 10 min. The solution was allowed to stand at 3° C. overnight. The reaction mixture was cooled to 0° C. and anhydrous Et$_2$O (25 mL) was added. The cold solution was filtered, and the imidate collected was dissolved in H$_2$O (15 mL). The solution was heated to 50° C. for 6 h. The mixture was then cooled, and extracted with EtOAc. The combined extracts were dried (MgSO$_4$), filtered and evaporated to afford 0.34 g (71%) of 58a.

EXAMPLE 7

2-[3-(3-Bromo-phenoxy)-4-chloro-benzyl]-6-methyl-4H-[1,3,4]oxadiazin-5-one (I-4)

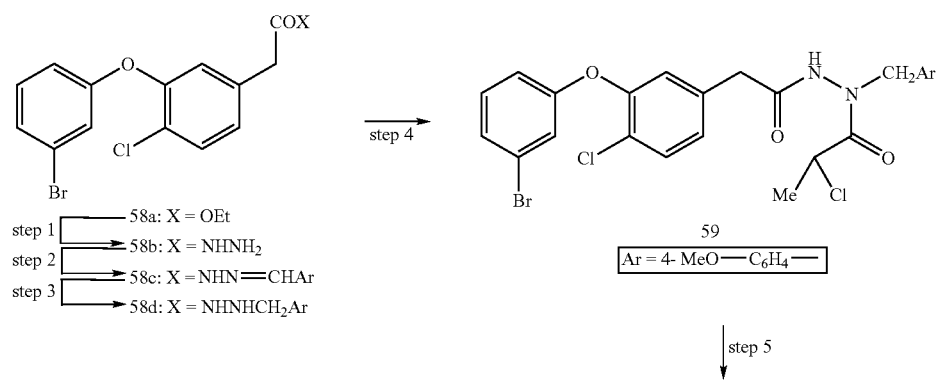

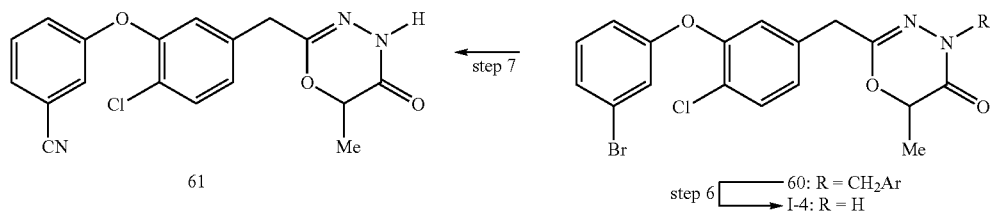

[3-(3-Bromo-phenoxy)-4-chloro-phenyl]-acetic acid ethyl ester 58a was prepared as described in Example 6.

step 1—To a mixture of 58a (585 mg, 1.40 mmol) and hydrazine (85% in water, 1.8 mL, 49 mmol) was added EtOH (5.5 mL). The solution was heated at reflux for 4 h and concentrated in vacuo. The crude product was recrystallized with 10 mL of MeOH to afford 370 mg (65%) of 58b as a white solid which was used without any further purification.

step 2—To a suspension of 58b (360 mg, 0.88 mmol) in EtOH (5.9 mL) was added p-anisaldehyde (0.11 mL, 0.93 mmol) and resulting mixture maintained under Ar and heated at reflux for 2 h then cooled to RT. The reaction mixture was diluted with ether (20 mL) and stored at 0° C. After 24 h, the precipitate was collected and dried to afford 417 mg (90%) of 58c as a white solid.

step 3—To an ice-cold solution of 58c (414 mg, 0.79 mmol) and TFA (1.3 mL) maintained under a $N_2$ atmosphere was added $Et_3SiH$ (0.25 mL, 1.6 mmol) via syringe. The solution was stirred at 0° C. for 1 h, concentrated in vacuo and re-dissolved in ether (10 mL). The mixture was washed with water (10 mL), saturated aqueous $NaHCO_3$ (10 mL), and brine (5 mL). The organic phase was dried ($MgSO_4$), filtered and concentrated. The crude product was purified by $SiO_2$ chromatography eluting with a MeOH/DCM gradient to afford 400 mg (96%) of 58d as a white solid.

step 4—To a solution of 58d (223 mg, 0.42 mmol) and anhydrous dioxane (4.2 mL) maintained under a $N_2$ atmosphere was added 2-chloro-propionyl chloride (46 μL, 0.46 mmol) and the reaction mixture was stirred stir at RT for 1 h. The mixture was concentrated in vacuo, re-dissolved in DCM (20 mL) and washed with brine (5 mL). The solution was dried ($MgSO_4$), filtered and concentrated in vacuo to afford 256 mg (98%) of 59 as a clear oil which was used without any further purification.

step 5—To a solution of 59 (256 mg, 0.41 mmol) and anhydrous MeCN (4.1 mL) under an $N_2$ atmosphere was added DBU (62 uL, 0.41 mmol) over one minute via syringe. The solution was stirred at RT for 1 h, then poured into saturated aqueous $NH_4Cl$ (10 mL) and extracted with EtOAc (60 mL). The organic layer was washed with brine (5 mL), dried ($MgSO_4$), filtered and concentrated in vacuo to afford 240 mg (99%) of 60 as a white solid step 6—A oven-dried round-bottom flask was flushed with Ar and charged with the oxadiazinone 60 (240 mg, 0.41 mmol) and $AlCl_3$ (220 mg, 1.6 mmol). To this was added anhydrous anisole (4.0 mL) and the solution was stirred under argon at RT for 18 h. The reaction was quenched with 5% aqueous HCl (25 mL) and extracted with EtOAc (60 mL). The organic layer was washed with brine (10 mL), dried ($MgSO_4$), filtered and concentrated in vacuo. The crude product was purified by $SiO_2$ chromatography eluting with MeOH/DCM to yield 190 mg (99%) of I-4 as a white solid.

2-[3-(3-Bromo-phenoxy)-4-chloro-benzyl]-6-ethyl-4H-[1,3,4]oxadiazin-5-one(I-12) was prepared by the procedure described in Example 7 except in step 4, 2-chloropropionyl chloride was replaced by 2-chlorobutyroyl chloride. 3-[2-Chloro-5-(6-ethyl-5-oxo-5,6-dihydro4H-[1,3,4]oxadiazin-2-ylmethyl)-phenoxy]-benzonitrile (I-14) was prepared by cyanation of I-12 as described in step 7 of Example 1.

2-[3-(3-Bromo-phenoxy)4-chloro-benzyl]-6,6-dimethyl-4H-[1,3,4]oxadiazin-5-one (I-11) was prepared by the procedure described in Example 7 except in step 4, 2-chloropropionyl chloride was replaced by 2-bromo-2-methyl-propionyl bromide.

3-[2-Chloro-5-(6,6-dimethyl-5-oxo-5,6-dihydro-4H-[1,3,4]oxadiazin-2-ylmethyl)-phenoxy]-benzonitrile (I-13) was prepared by cyanation of I-11 as described in step 7 of Example 1.

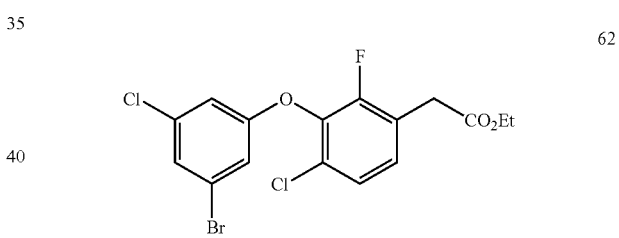

2-[3-(3-Bromo-5-chloro-phenoxy)-4-chloro-2-fluoro-benzyl]-6-methyl-4H-[1,3,4]oxadiazin-5-one (I-6) was prepared analogously. [3-(3-Bromo-5-chloro-phenoxy)-4-chloro-2-fluoro-phenyl]-acetic acid ethyl ester 62 was prepared by the procedure described in steps 1-4 of Example 1 except in step 1,3,5-dibromophenol was replaced with 3-bromo-5-chlorophenol and in step 2, tert-butyl cyanoacetate was replaced by tert-butyl ethyl malonate. 3-Chloro-5-[6-chloro-2-fluoro-3-(6-methyl-5-oxo-5,6-dihydro-4H-[1,3,4]oxadiazin-2-ylmethyl)-phenoxy]-benzonitrile (I-8) was prepared by cyanation of I-6 as described in step 7 of Example 1.

2-[4-Chloro-3-(3,5-dibromo-phenoxy)-2-fluoro-benzyl]-6-methyl-4H-[1,3,4]oxadiazin-5-one (I-7) and 5-[6-chloro-2-fluoro-3-(6-methyl-5-oxo-5,6-dihydro-4H-[1,3,4]oxadiazin-2-ylmethyl)-phenoxy]-isophthalonitrile (I-9) were prepared in the same fashion as I-6 and I-8 except 3,5-dibromophenol was used as described in step 1 of Example 1 which afforded [4-chloro-3-(3,5-dibromo-phenoxy)-2-fluoro-phenyl]-acetic acid ethyl ester. The ester was converted to I-7 as described in steps 4-6 of Example 7.

EXAMPLE 8

(S)-6-[3-(3-Bromo-phenoxy)4-chloro-benzyl]-4-methyl-4,5-dihydro-2H-pyridazin-3-one (I-20) and 3-[2-chloro-5-((S)-5-methyl-6-oxo-1,4,5,6-tetrahydro-pyridazin-3-ylmethyl)-phenoxy]-benzonitrile (I-21)

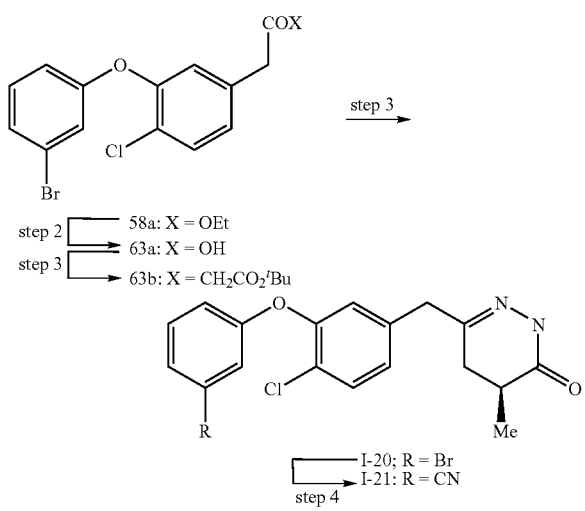

step 1—To a solution of the 58a (2.80 g, 7.57 mmol) in EtOH (16 mL) was added a solution of NaOH (364 mg, 9.09 mmol) in H$_2$O (4 mL). The solution was stirred for 15 h, and the EtOH was removed in vacuo. Water (30 mL) was added, the solution was washed with Et$_2$O (20 mL), the solution was acidified to pH 1 and extracted with Et$_2$O. The organic extracts were washed with brine and dried (MgSO$_4$). The volatile materials were evaporated to afford 2.36 g (92%) of 63a.

step 2—To a ice-cold solution of 63a (1.86 g, 5.44 mmol) in anhydrous THF (16 mL) was added 1,1'-carbonyldiimidazole (1.06 g, 6.5 mmol). The solution was stirred for 1 h. In a separate flask, isopropylmagnesium chloride (8.17 mL of a 2 M solution in Et$_2$O, 16.3 mmol) was added dropwise to a cold (0C) solution of the tert-butyl ethyl malonate (1.26 mL, 8.17 mmol) in anhydrous THF (10 mL). The solution containing the malonate was heated to 45° C. for 45 min, cooled to RT, and then added slowly to the cold solution of the acylimidazole. The combined solutions were stirred for 16 h, added slowly to 10% HCl solution, and extracted with Et$_2$O. The combined extracts were washed with brine and dried (MgSO$_4$). The crude product was purified by SiO$_2$ chromatography eluting with an EtOAc/hexane gradient (0% to 10% EtOAc) which afforded 1.81 g (76%) of 63b.

step 3—To an ice-cold solution of 63b (885 mg, 2.01 mmol) in anhydrous THF was added NaH (88 mg, 60% suspension in mineral oil, 2.21 mmol). After 15 min, ethyl S-2-trifluoromethylsulfonyloxy-propionate (431 µL, 2.31 mmol) was added, and the reaction mixture was warmed to RT and stirred for 16 h. The reaction mixture was added slowly to 10% HCl, and extracted with Et$_2$O. The combined organics were washed with brine and dried (MgSO$_4$). The volatile materials were removed in vacuo, and the residue was dissolved in TFA (8 mL) and stirred for 2 h. The TFA was removed in vacuo, the residue suspended in benzene (10 mL), and heated to reflux for 2 h. The volatile materials were removed, and the residue was purified by SiO2 chromatography eluting with an EtOAc/hexanes gradient (0% to 25% EtOAc) to afford the desired keto-ester. To a solution of this keto-ester in EtOH was added hydrazine (120 uL, 2.45 mmol), and the mixture was heated to reflux for 2 h. The reaction was cooled to RT, and the volatile materials were evaporated in vacuo. The residue was dissolved in EtOAc, washed with water, brine, and dried (MgSO$_4$). Evaporation of the volatile materials and purification of the residue by SiO$_2$ chromatography afforded 430 mg (52%) of the dihydropyridazinone I-20: (ESI MS) (M+H)=407.

step 4—A solution of I-20 (213 mg, 0.52 mmol), Zn(CN)$_2$ (37 mg, 0.31 mmol), Pd(PPh$_3$)$_4$ (120 mg, 0.10 mmol) in anhydrous DMF (3 mL) was heated to 80° C. under a N$_2$ atmosphere. The reaction was cooled to RT, poured into 2M NH$_4$OH, and extracted with EtOAc. The combined extracts were washed with water, brine, and dried (MgSO$_4$). Evaporation of the volatile materials and purification of the residue by SiO$_2$ chromatography eluting with an EtOAc/hexanes gradient (0% to 100% EtOAc) afforded 156 mg (84%) of I-21: (ESI MS) (M+H)=354.

(S)-6-[3-(3-Bromo-5-chloro-phenoxy)-4-chloro-2-fluoro-benzyl]-4-methyl-4,5-dihydro-2H-pyridazin-3-one (I-23) and 3-chloro-5-[6-chloro-2-fluoro-3-((S)-5-methyl-6-oxo-1,4,5,6-tetrahydro-pyridazin-3-ylmethyl)-phenoxy]-benzonitrile (I-22) were prepared by the procedure of Example 8 except 58a was replaced by [3-(3-bromo-5-chloro-phenoxy)-4-chloro-2-fluoro-phenyl]-acetic acid ethyl ester in step 1.

EXAMPLE 9

3-[6-Bromo-2-fluoro-3-((R)-5-methyl-6-oxo-1,4,5,6-tetrahydro-[1,2,4]triazin-3-ylmethyl)-phenoxy]-5-difluoromethyl-benzonitrile (I-25)

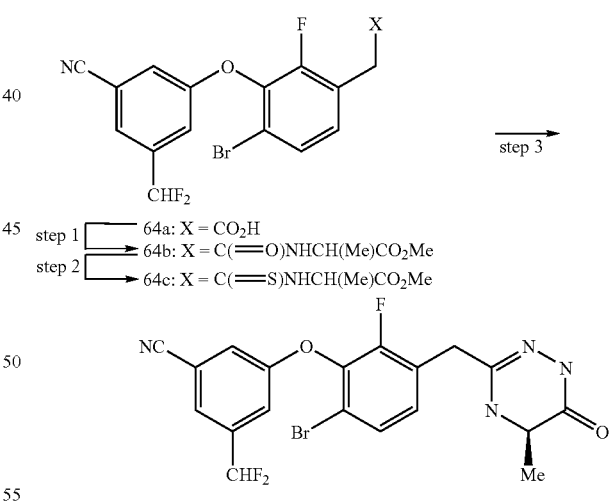

step 1—TEA (0.73 mL, 5.25 mmol) was added to a solution of D-alanine methyl ester hydrochloride (0.73 g, 5.25 mmol), DCC (1.08 g, 5.25 mmol), HOBt (0.71 g, 5.25 mmol), 64a (2.10 g, 5.247 mmol) dissolved in DMF (5 mL) in DCM (50 mL) and the mixture was stirred at RT under a N$_2$ atmosphere 14 h. The reaction was quenched by the addition of water. The organic phase was separated, washed with brine, dried (MgSO$_4$) and evaporated in vacuo. The residue was purified by SiO$_2$ chromatography eluting with 20% EtOAc/hexane to afford 0.90 g (36%) of 64b as an off-white solid.

step 2—A mixture of (R) 64b (0.90 g, 1.91 mmol), Lawesson's reagent (0.38 g, .0.95 mmol) in benzene (30 mL) was maintained under a $N_2$ atmosphere and heated at 90° C. for 14 h. The reaction mixture was cooled to RT and then evaporated to dryness. The crude product was purified by $SiO_2$ chromatography eluting with an EtOAc/hexane gradient (5 to 20% EtOAc) to afford 0.56 g (58%) of (R) 64c as an oil.

step 3—Aqueous hydrazine (0.20 mL, 3.30 mmol) was added to 64c (0.56 g, 1.12 mmol) in dioxane (30 mL) and the mixture was stirred at 90° C. for 6 h, then at RT for 36 h. The reaction mixture was evaporated and the crude residue purified by $SiO_2$ chromatography eluting with a MeOH/DCM gradient (2 to 10% MeOH DCM) and then crystallized from IPA to afford 0.30 g (55%) of I-25 as a white solid (0.30 g, 55%): mp 183.7-185.8° C.; m/z=467 (MH+).

EXAMPLE 10

6-(4-Chloro-3-phenoxy-benzyl)-4,5-dihydro-2H-pyridazin-3-one (I-24)

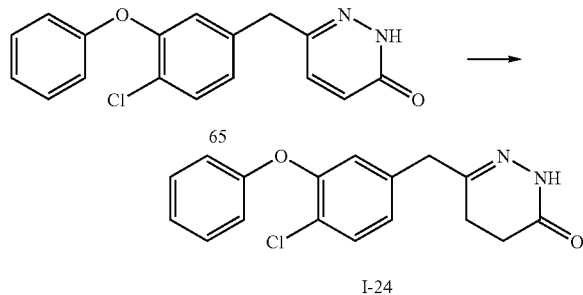

6-(4-Chloro-3-phenoxy-benzyl)-2H-pyridazin-3-one is prepared by combining 28 (1.0 equivalent), benzeneboronic acid (2.5 equivalents), cupric acetate (1.1 equivalents), 4 Å molecular sieves (1 g), and $CH_2Cl_2$ (25 mL), TEA (5 equivalents) and stirring the resulting mixture overnight. Additional benzeneboronic acid is added and stirring is continued until starting material is consumed. The reaction mixture is filtered through a pad of CELITE®) and is washed with $CHCl_3$. The combined organic filtrates are evaporated. The crude product was purified by $SiO_2$ chromatography with silica gel eluting with a hexane/EtOAc gradient (0 to 25% EtOAc) to yield 65.

A solution of 15% $TiCl_3$ in aqueous HCl (12 mL) was added to a solution of 65 (0.38g, 1.2 mmol) in MeCN (16 mL). The solution was heated to 50° C. for 5 h and then cooled to RT and stirred for 12 h. The mixture was poured into a solution of 10% NaOH and extracted with EtOAc. The crude product was purified by $SiO_2$ chromatography eluting with an EtOAc/hexane gradient (50 to 75% EtOAc) to afford 0.045 g (12%) of I-24 as a white solid (0.045 g, 12%).

EXAMPLE 11

HIV Reverse Transcriptase Assay: Inhibitor $IC_{50}$ determination

HIV-1 RT assay was carried out in 96-well Millipore MultiScreen MADVNOB50 plates using purified recombinant enzyme and a poly(rA)/oligo(dT)$_{16}$ template-primer in a total volume of 50 μL. The assay constituents were 50 mM Tris/HCl, 50 mM NaCl, 1 mM EDTA, 6 mM $MgCl_2$, 5 μM dTTP, 0.15 μCi [$^3$H] dTTP, 5 μg/ml poly (rA) pre annealed to 2.5 μg/ml oligo (dT)$_{16}$ and a range of inhibitor concentrations in a final concentration of 10% DMSO. Reactions were initiated by adding 4 nM HIV-1 RT and after incubation at 37° C. for 30 min, they were stopped by the addition of 50 μl ice cold 20% TCA and allowed to precipitate at 4° C. for 30 min. The precipitates were collected by applying vacuum to the plate and sequentially washing with 3×200 μl of 10% TCA and 2×200 μl 70% ethanol. Finally, the plates were dried and radioactivity counted in a Packard TopCounter after the addition of 25 μl scintillation fluid per well. $IC_{50}$'s were calculated by plotting % inhibition versus $log_{10}$ inhibitor concentrations.

EXAMPLE 12

Anti-viral Assay

Anti-viral assays were carried out by the method described by R. E. Pauwels et al. *J Virol. Methods* 1988 20(4):309-322.

TABLE 3

| Compound # | RT inhibition IC50 (μM) | Anti-Viral Assay EC$_{50}$ (μM) |
| --- | --- | --- |
| I-5 | 0.032 | 0.0122 |
| I-15 | 0.011 | 0.0083 |

EXAMPLE 13

Pharmaceutical Compositions

Pharmaceutical compositions of the subject Compounds for administration via several routes were prepared as described in this Example.

| Composition for Oral Administration (A) | |
| --- | --- |
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
| --- | --- |
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
| --- | --- |
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
| --- | --- |
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound according to formula I:

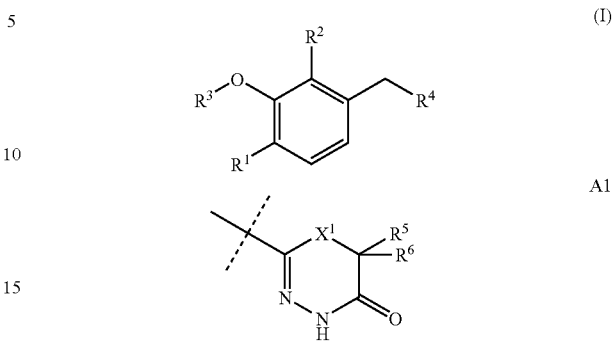

wherein
$X^1$ is $NR^8$;
$R^1$ is hydrogen, halogen, $C_{1-6}$ alkyl or $C_{1-6}$ alkoxy;
$R^2$ is hydrogen or halogen;
$R^3$ is phenyl optionally substituted with one to three substituents independently selected from the group consisting of $C_{1-6}$ alkyl, $C_{1-6}$ haloalkyl, $C_{3-8}$ cycloalkyl, halogen, cyano or nitro;
$R^4$ is A1;
$R^5$ and $R^6$ are independently hydrogen, $C_{1-10}$ alkyl, $C_{1-6}$ haloalkyl, hydroxy-$C_{1-6}$ alkyl or phenyl optionally substituted with 1 to 3 groups independently selected in each occurrence from the group consisting of $C_{1-6}$ alkyl, $C_{1-6}$ alkoxy, $C_{1-6}$ haloalkyl, halogen, hydroxy, nitro and cyano, or, $R^5$ and $R^6$ together are $(CH_2)_n$;
$R^7$ is hydrogen, $C_{1-10}$ alkyl or phenyl;
$R^8$ is hydrogen or $C_{1-6}$ alkyl;
n is 2 to 4; or,
a pharmaceutically acceptable salts thereof.

2. A compound according to claim 1 wherein $R^4$ is A1 and $R^8$ is hydrogen.

3. A compound according to claim 2 wherein $R^1$ is bromo, chloro, methyl or ethyl and $R^2$ is hydrogen or fluoride.

4. A compound according to claim 3 wherein $R^3$ is phenyl substituted with one or two substituents independently selected from the group consisting of halogen, cyano and haloalkyl.

5. A compound according to claim 3 wherein $R^3$ is a 3,5-disubstituted phenyl.

6. A compound according to claim 3 wherein $R^3$ is phenyl substituted with one or two substituents independently selected from the group consisting of halogen, cyano and haloalkyl.

7. A method for treating or preventing an human immunodeficiency virus (HIV) infection, or treating AIDS or ARC, in a patient in need thereof which comprises administering to the patient a therapeutically effective amount of a compound of claim 1.

8. A method according to claim 7 further comprising co-administering at least one compound selected from the group consisting of HIV nucleoside reverse transcriptase inhibitors, HIV non-nucleoside reverse transcriptase inhibitors, HIV protease inhibitors and viral fusion inhibitors.

9. A method according to claim 8 wherein the non-reverse transcriptase inhibitor is selected from the group consisting of efavirenz, nevirapine or delavirdine, and/or the nucleoside reverse transcriptase inhibitor is selected from the group consisting of zidovudine, didanosin, zalcitabine, stavudine, lamivudine, abacavir, adefovir and dipivoxil, and/or the protease inhibitor is selected from the group consisting of saquinavir, ritonavir, nelfinavir, indinavir, amprenavir and lopinavir and and/or the vial fusion inhibitor T20.

10. A method for inhibiting a retrovirus reverse transcriptase a patient in need thereof comprising administering a therapeutically effective amount of a compound according to claim 1.

11. A method according to claim 10 wherein said retrovirus reverse transcriptase exhibits at least one mutation compared to wild type virus.

12. A method according to claim 7 wherein said patient is infected with at least one strain of HIV that exhibits reduced susceptibility to efavirenz, nevirapine or delavirdine.

13. A pharmaceutical composition for treating a human immunodeficiency virus (HIV) infection, or treating AIDS or ARC comprising a compound according to claim 1 admixed with at least one pharmaceutically acceptable carrier, diluent or excipient.

14. A process for preparing a compound of claim 1 wherein $R^4$ is A1, $X^1$ is $NR^8$, $R^8$ is hydrogen, and $R^3$, $R^5$, $R^6$, $R^7$, and n are as defined in claim 1 comprising the steps of:

(i) contacting a phenylacetic acid compound II with an amino acid ester in the presence of a coupling reagent to produce III;

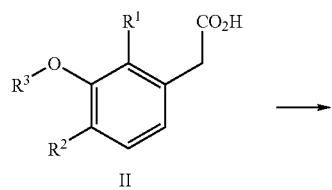

II

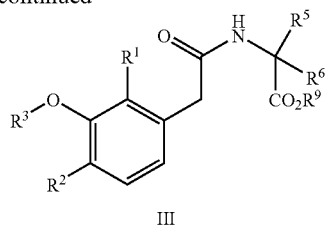

III (ii) contacting III with Lawesson's reagent to afford IV; and,

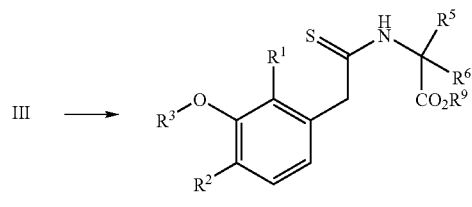

(iii) contacting IV with hydrazine to produce a compound of formula I wherein $R^4$ is A1 and $X^1$ is $NR^8$ and $R^8$ is hydrogen.

* * * * *